United States Patent
Stulen

(10) Patent No.: US 8,882,791 B2
(45) Date of Patent: Nov. 11, 2014

(54) ULTRASONIC SURGICAL INSTRUMENTS

(75) Inventor: Foster B. Stulen, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 605 days.

(21) Appl. No.: 11/881,645

(22) Filed: Jul. 27, 2007

(65) Prior Publication Data

US 2009/0030439 A1    Jan. 29, 2009

(51) Int. Cl.
    *A61B 17/32*        (2006.01)
    *A61B 17/3203*      (2006.01)
    *A61B 17/22*        (2006.01)

(52) U.S. Cl.
    CPC ..... *A61B 17/320068* (2013.01); *A61B 17/3203* (2013.01); *A61B 2017/320072* (2013.01); *A61B 2017/32035* (2013.01); *A61B 2017/22082* (2013.01); *A61B 17/320092* (2013.01)
    USPC ........................................................ 606/169

(58) Field of Classification Search
USPC ................. 600/184; 604/22, 46; 606/39, 167, 606/169–171, 32, 45, 159; 433/86, 433/118–121, 165, 224; 601/2–4
See application file for complete search history.

(56) References Cited

U.S. PATENT DOCUMENTS

| | | | |
|---|---|---|---|
| 2,704,333 A * | 3/1955 | Calosi et al. | .......... 310/26 |
| 2,736,960 A | 3/1956 | Armstrong | |
| 2,849,788 A | 9/1958 | Creek | |
| RE25,033 E * | 8/1961 | Balamuth et al. | .......... 451/36 |
| 3,015,961 A | 1/1962 | Roney | |
| 3,513,848 A | 5/1970 | Winston et al. | |
| 3,526,219 A | 9/1970 | Balamuth | |
| 3,614,484 A | 10/1971 | Shoh | |
| 3,636,943 A * | 1/1972 | Balamuth | .......... 601/2 |
| 3,776,238 A | 12/1973 | Peyman et al. | |
| 3,805,787 A | 4/1974 | Banko | |
| 3,830,098 A | 8/1974 | Antonevich | |
| 3,854,737 A | 12/1974 | Gilliam, Sr. | |
| 3,862,630 A | 1/1975 | Balamuth | |
| 3,900,823 A | 8/1975 | Sokal et al. | |

(Continued)

FOREIGN PATENT DOCUMENTS

| | | |
|---|---|---|
| CN | 1634601 A | 7/2005 |
| CN | 1640365 A | 7/2005 |

(Continued)

OTHER PUBLICATIONS

AST Products, Inc., "Principles of Video Contact Angle Analysis," 20 pages, (date unknown).

(Continued)

*Primary Examiner* — Ashley Fishback

(57) ABSTRACT

A surgical instrument includes a transducer configured to produce vibrations at a predetermined frequency. The transducer is configured to produce vibrations at a predetermined frequency. An ultrasonic blade extends along the longitudinal axis and is coupled to the transducer. The ultrasonic blade includes a body having a proximal end and a distal end. The distal end is movable relative to the longitudinal axis by the vibrations produced by the transducer. The body includes a treatment region that extends from the proximal end to the distal end. The body includes surface coatings to prevent the formation of a thin layer of fluid on the body which may be atomized thus creating a mist. The body may also include a bore configured to emit a spray which will also prevent the formation of thin layer of fluid on the body.

10 Claims, 21 Drawing Sheets

(56) References Cited

U.S. PATENT DOCUMENTS

| | | | |
|---|---|---|---|
| 3,918,442 A | 11/1975 | Nikolaev et al. | |
| 3,946,738 A | 3/1976 | Newton et al. | |
| 3,955,859 A | 5/1976 | Stella et al. | |
| 3,956,826 A | 5/1976 | Perdreaux, Jr. | |
| 4,156,187 A | 5/1979 | Murry et al. | |
| 4,188,927 A | 2/1980 | Harris | |
| 4,200,106 A | 4/1980 | Douvas et al. | |
| 4,306,570 A | 12/1981 | Matthews | |
| 4,445,063 A | 4/1984 | Smith | |
| 4,491,132 A | 1/1985 | Aikins | |
| 4,574,615 A | 3/1986 | Bower et al. | |
| 4,617,927 A | 10/1986 | Manes | |
| 4,633,119 A | 12/1986 | Thompson | |
| 4,634,420 A | 1/1987 | Spinosa et al. | |
| 4,640,279 A * | 2/1987 | Beard | 606/28 |
| 4,649,919 A | 3/1987 | Thimsen et al. | |
| 4,708,127 A | 11/1987 | Abdelghani | |
| 4,712,722 A | 12/1987 | Hood et al. | |
| 4,827,911 A | 5/1989 | Broadwin et al. | |
| 4,832,683 A | 5/1989 | Idemoto et al. | |
| 4,838,853 A | 6/1989 | Parisi | |
| 4,850,354 A | 7/1989 | McGurk-Burleson et al. | |
| 4,865,159 A | 9/1989 | Jamison | |
| 4,896,009 A | 1/1990 | Pawlowski | |
| 4,903,696 A | 2/1990 | Stasz et al. | |
| 4,922,902 A | 5/1990 | Wuchinich et al. | |
| 4,965,532 A | 10/1990 | Sakurai | |
| 4,979,952 A | 12/1990 | Kubota et al. | |
| 4,981,756 A | 1/1991 | Rhandhawa | |
| 5,026,387 A | 6/1991 | Thomas | |
| 5,112,300 A | 5/1992 | Ureche | |
| 5,123,903 A | 6/1992 | Quaid et al. | |
| 5,126,618 A | 6/1992 | Takahashi et al. | |
| 5,162,044 A | 11/1992 | Gahn et al. | |
| 5,167,725 A | 12/1992 | Clark et al. | |
| D332,660 S | 1/1993 | Rawson et al. | |
| 5,176,695 A | 1/1993 | Dulebohn | |
| 5,184,605 A | 2/1993 | Grzeszykowski | |
| 5,213,569 A | 5/1993 | Davis | |
| 5,221,282 A | 6/1993 | Wuchinich | |
| 5,226,909 A | 7/1993 | Evans et al. | |
| 5,226,910 A | 7/1993 | Kajiyama et al. | |
| 5,241,236 A | 8/1993 | Sasaki et al. | |
| 5,257,988 A | 11/1993 | L'Esperance, Jr. | |
| 5,261,922 A | 11/1993 | Hood | |
| 5,263,957 A | 11/1993 | Davison | |
| 5,275,609 A | 1/1994 | Pingleton et al. | |
| 5,282,800 A | 2/1994 | Foshee et al. | |
| 5,304,115 A | 4/1994 | Pflueger et al. | |
| D347,474 S | 5/1994 | Olson | |
| 5,322,055 A | 6/1994 | Davison et al. | |
| 5,324,299 A | 6/1994 | Davison et al. | |
| 5,344,420 A | 9/1994 | Hilal et al. | |
| 5,346,502 A | 9/1994 | Estabrook et al. | |
| 5,357,423 A | 10/1994 | Weaver et al. | |
| 5,366,466 A | 11/1994 | Christian et al. | |
| D354,564 S | 1/1995 | Medema | |
| 5,381,067 A | 1/1995 | Greenstein et al. | |
| 5,403,312 A | 4/1995 | Yates et al. | |
| 5,411,481 A | 5/1995 | Allen et al. | |
| 5,419,761 A | 5/1995 | Narayanan et al. | |
| 5,421,829 A | 6/1995 | Olichney et al. | |
| 5,438,997 A | 8/1995 | Sieben et al. | |
| 5,449,370 A | 9/1995 | Vaitekunas | |
| 5,471,988 A | 12/1995 | Fujio et al. | |
| 5,483,501 A | 1/1996 | Park et al. | |
| 5,486,162 A | 1/1996 | Brumbach | |
| 5,500,216 A * | 3/1996 | Julian et al. | 424/401 |
| 5,501,654 A | 3/1996 | Failla et al. | |
| 5,505,693 A | 4/1996 | Mackool | |
| 5,527,331 A | 6/1996 | Kresch et al. | |
| 5,562,609 A | 10/1996 | Brumbach | |
| 5,562,610 A | 10/1996 | Brumbach | |
| 5,601,601 A | 2/1997 | Tal et al. | |
| 5,603,773 A | 2/1997 | Campbell | |
| 5,607,436 A | 3/1997 | Pratt et al. | |
| 5,618,492 A * | 4/1997 | Auten et al. | 422/22 |
| 5,628,760 A * | 5/1997 | Knoepfler | 606/170 |
| 5,630,420 A | 5/1997 | Vaitekunas | |
| D381,077 S | 7/1997 | Hunt | |
| 5,651,780 A | 7/1997 | Jackson et al. | |
| 5,653,713 A | 8/1997 | Michelson | |
| 5,669,922 A | 9/1997 | Hood | |
| 5,674,235 A | 10/1997 | Parisi | |
| 5,690,269 A | 11/1997 | Bolanos et al. | |
| 5,694,936 A | 12/1997 | Fujimoto et al. | |
| 5,713,896 A | 2/1998 | Nardella | |
| 5,730,752 A | 3/1998 | Alden et al. | |
| 5,733,074 A | 3/1998 | Stöck et al. | |
| 5,741,226 A | 4/1998 | Strukel et al. | |
| 5,792,135 A | 8/1998 | Madhani et al. | |
| 5,810,859 A | 9/1998 | DiMatteo et al. | |
| 5,817,084 A | 10/1998 | Jensen | |
| 5,827,323 A | 10/1998 | Klieman et al. | |
| 5,828,160 A | 10/1998 | Sugishita | |
| 5,836,897 A | 11/1998 | Sakurai et al. | |
| 5,843,109 A | 12/1998 | Mehta et al. | |
| 5,878,193 A | 3/1999 | Wang et al. | |
| 5,879,364 A | 3/1999 | Bromfield et al. | |
| 5,893,835 A | 4/1999 | Witt et al. | |
| 5,897,569 A | 4/1999 | Kellogg et al. | |
| 5,906,628 A | 5/1999 | Miyawaki et al. | |
| 5,935,143 A | 8/1999 | Hood | |
| 5,935,144 A | 8/1999 | Estabrook | |
| 5,938,633 A | 8/1999 | Beaupre | |
| 5,944,718 A | 8/1999 | Austin et al. | |
| 5,944,737 A | 8/1999 | Tsonton et al. | |
| 5,954,736 A | 9/1999 | Bishop et al. | |
| 5,954,746 A | 9/1999 | Holthaus et al. | |
| 5,957,882 A | 9/1999 | Nita et al. | |
| 5,957,943 A | 9/1999 | Vaitekunas | |
| 5,968,007 A | 10/1999 | Simon et al. | |
| 5,968,060 A | 10/1999 | Kellogg | |
| D416,089 S | 11/1999 | Barton et al. | |
| 5,980,510 A | 11/1999 | Tsonton et al. | |
| 5,989,274 A | 11/1999 | Davison et al. | |
| 5,989,275 A | 11/1999 | Estabrook et al. | |
| 5,993,972 A | 11/1999 | Reich et al. | |
| 6,024,741 A | 2/2000 | Williamson, IV et al. | |
| 6,033,375 A | 3/2000 | Brumbach | |
| 6,051,010 A | 4/2000 | DiMatteo et al. | |
| 6,056,735 A | 5/2000 | Okada et al. | |
| 6,063,098 A | 5/2000 | Houser et al. | |
| 6,066,132 A | 5/2000 | Chen et al. | |
| 6,068,647 A | 5/2000 | Witt et al. | |
| 6,077,285 A | 6/2000 | Boukhny | |
| 6,083,191 A | 7/2000 | Rose | |
| 6,086,584 A | 7/2000 | Miller | |
| 6,090,120 A | 7/2000 | Wright et al. | |
| 6,109,500 A | 8/2000 | Alli et al. | |
| 6,110,127 A | 8/2000 | Suzuki | |
| 6,113,594 A | 9/2000 | Savage | |
| 6,129,735 A | 10/2000 | Okada et al. | |
| 6,132,368 A | 10/2000 | Cooper | |
| 6,139,320 A | 10/2000 | Hahn | |
| 6,139,561 A | 10/2000 | Shibata et al. | |
| 6,142,615 A | 11/2000 | Qiu et al. | |
| 6,152,902 A | 11/2000 | Christian et al. | |
| 6,159,160 A | 12/2000 | Hsei et al. | |
| 6,159,175 A | 12/2000 | Strukel et al. | |
| 6,204,592 B1 | 3/2001 | Hur | |
| 6,206,844 B1 | 3/2001 | Reichel et al. | |
| 6,210,403 B1 | 4/2001 | Klicek | |
| 6,214,023 B1 | 4/2001 | Whipple et al. | |
| 6,231,565 B1 | 5/2001 | Tovey et al. | |
| 6,233,476 B1 | 5/2001 | Strommer et al. | |
| 6,238,366 B1 | 5/2001 | Savage et al. | |
| 6,252,110 B1 | 6/2001 | Uemura et al. | |
| D444,365 S | 7/2001 | Bass et al. | |
| 6,254,623 B1 | 7/2001 | Haibel, Jr. et al. | |
| 6,258,034 B1 | 7/2001 | Hanafy | |
| 6,267,761 B1 | 7/2001 | Ryan | |
| 6,270,831 B2 | 8/2001 | Kumar et al. | |
| 6,273,852 B1 | 8/2001 | Lehe et al. | |

(56) References Cited

U.S. PATENT DOCUMENTS

| | | |
|---|---|---|
| 6,274,963 B1 | 8/2001 | Estabrook et al. |
| 6,277,115 B1 | 8/2001 | Saadat |
| 6,278,218 B1 | 8/2001 | Madan et al. |
| 6,283,981 B1 | 9/2001 | Beaupre |
| 6,309,400 B2 | 10/2001 | Beaupre |
| 6,319,221 B1 | 11/2001 | Savage et al. |
| 6,325,811 B1 | 12/2001 | Messerly |
| 6,328,751 B1 | 12/2001 | Beaupre |
| 6,340,352 B1 | 1/2002 | Okada et al. |
| 6,352,532 B1 | 3/2002 | Kramer et al. |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,387,109 B1 | 5/2002 | Davison et al. |
| 6,388,657 B1 | 5/2002 | Natoli |
| 6,391,042 B1 | 5/2002 | Cimino |
| 6,405,733 B1 | 6/2002 | Fogarty et al. |
| 6,416,486 B1 | 7/2002 | Wampler |
| 6,423,073 B2 | 7/2002 | Bowman |
| 6,423,082 B1 | 7/2002 | Houser et al. |
| 6,428,539 B1 | 8/2002 | Baxter et al. |
| 6,432,118 B1 | 8/2002 | Messerly |
| 6,436,114 B1 | 8/2002 | Novak et al. |
| 6,436,115 B1 | 8/2002 | Beaupre |
| 6,443,969 B1 | 9/2002 | Novak et al. |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,485,490 B2 | 11/2002 | Wampler et al. |
| 6,491,708 B2 | 12/2002 | Madan et al. |
| 6,497,715 B2 | 12/2002 | Satou |
| 6,500,176 B1 | 12/2002 | Truckai et al. |
| 6,500,188 B2 | 12/2002 | Harper et al. |
| 6,524,316 B1 | 2/2003 | Nicholson et al. |
| 6,527,736 B1 | 3/2003 | Attinger et al. |
| 6,533,784 B2 | 3/2003 | Truckai et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,561,983 B2 | 5/2003 | Cronin et al. |
| 6,572,632 B2 | 6/2003 | Zisterer et al. |
| 6,575,969 B1 | 6/2003 | Rittman, III et al. |
| 6,582,451 B1 | 6/2003 | Marucci et al. |
| 6,589,200 B1 | 7/2003 | Schwemberger et al. |
| 6,589,239 B2 | 7/2003 | Khandkar et al. |
| 6,616,450 B2 | 9/2003 | Mossle et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,656,177 B2 | 12/2003 | Truckai et al. |
| 6,662,127 B2 | 12/2003 | Wiener et al. |
| 6,663,941 B2 | 12/2003 | Brown et al. |
| 6,669,690 B1 | 12/2003 | Okada et al. |
| 6,676,660 B2 | 1/2004 | Wampler et al. |
| 6,678,621 B2 | 1/2004 | Wiener et al. |
| 6,679,899 B2 | 1/2004 | Wiener et al. |
| 6,682,544 B2 | 1/2004 | Mastri et al. |
| 6,689,146 B1 | 2/2004 | Himes |
| 6,716,215 B1 | 4/2004 | David et al. |
| 6,731,047 B2 | 5/2004 | Kauf et al. |
| 6,733,506 B1 | 5/2004 | McDevitt et al. |
| 6,762,535 B2 | 7/2004 | Take et al. |
| 6,770,072 B1 | 8/2004 | Truckai et al. |
| 6,773,443 B2 | 8/2004 | Truwit et al. |
| 6,773,444 B2 | 8/2004 | Messerly |
| 6,783,524 B2 | 8/2004 | Anderson et al. |
| 6,786,382 B1 | 9/2004 | Hoffman |
| 6,786,383 B2 | 9/2004 | Stegelmann |
| 6,790,216 B1 | 9/2004 | Ishikawa |
| 6,802,843 B2 | 10/2004 | Truckai et al. |
| 6,828,712 B2 | 12/2004 | Battaglin et al. |
| 6,869,439 B2 | 3/2005 | White et al. |
| 6,875,220 B2 | 4/2005 | Du et al. |
| 6,905,497 B2 | 6/2005 | Truckai et al. |
| 6,908,472 B2 | 6/2005 | Wiener et al. |
| 6,913,579 B2 | 7/2005 | Truckai et al. |
| 6,926,716 B2 | 8/2005 | Baker et al. |
| 6,929,632 B2 | 8/2005 | Nita et al. |
| 6,929,644 B2 | 8/2005 | Truckai et al. |
| D509,589 S | 9/2005 | Wells |
| 6,942,677 B2 | 9/2005 | Nita et al. |
| 6,945,981 B2 | 9/2005 | Donofrio et al. |
| D511,145 S | 11/2005 | Donofrio et al. |
| 6,976,844 B2 * | 12/2005 | Hickok et al. ............. 433/224 |
| 6,976,969 B2 | 12/2005 | Messerly |
| 6,977,495 B2 | 12/2005 | Donofrio |
| 6,984,220 B2 | 1/2006 | Wuchinich |
| 7,011,657 B2 | 3/2006 | Truckai et al. |
| 7,033,357 B2 | 4/2006 | Baxter et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,070,597 B2 | 7/2006 | Truckai et al. |
| 7,074,219 B2 | 7/2006 | Levine et al. |
| 7,077,039 B2 | 7/2006 | Gass et al. |
| 7,077,853 B2 | 7/2006 | Kramer et al. |
| 7,083,619 B2 | 8/2006 | Truckai et al. |
| 7,087,054 B2 | 8/2006 | Truckai et al. |
| 7,101,378 B2 | 9/2006 | Salameh et al. |
| 7,108,695 B2 | 9/2006 | Witt et al. |
| 7,112,201 B2 | 9/2006 | Truckai et al. |
| 7,118,564 B2 | 10/2006 | Ritchie et al. |
| 7,124,932 B2 | 10/2006 | Isaacson et al. |
| 7,125,409 B2 | 10/2006 | Truckai et al. |
| 7,135,018 B2 | 11/2006 | Ryan et al. |
| 7,135,030 B2 | 11/2006 | Schwemberger et al. |
| 7,153,315 B2 | 12/2006 | Miller |
| D536,093 S | 1/2007 | Nakajima et al. |
| 7,156,189 B1 | 1/2007 | Bar-Cohen et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,163,548 B2 | 1/2007 | Stulen et al. |
| 7,169,146 B2 | 1/2007 | Truckai et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,204,820 B2 | 4/2007 | Akahoshi |
| 7,220,951 B2 | 5/2007 | Truckai et al. |
| 7,223,229 B2 | 5/2007 | Inman et al. |
| 7,229,455 B2 | 6/2007 | Sakurai et al. |
| 7,273,483 B2 | 9/2007 | Wiener et al. |
| 7,309,849 B2 | 12/2007 | Truckai et al. |
| 7,311,709 B2 | 12/2007 | Truckai et al. |
| 7,317,955 B2 | 1/2008 | McGreevy |
| 7,326,236 B2 | 2/2008 | Andreas et al. |
| 7,331,410 B2 | 2/2008 | Yong et al. |
| 7,353,068 B2 | 4/2008 | Tanaka et al. |
| 7,354,440 B2 | 4/2008 | Truckai et al. |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,390,317 B2 | 6/2008 | Taylor et al. |
| 7,404,508 B2 | 7/2008 | Smith et al. |
| 7,408,288 B2 | 8/2008 | Hara |
| D576,725 S | 9/2008 | Shumer et al. |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,441,684 B2 | 10/2008 | Shelton, IV et al. |
| 7,455,208 B2 | 11/2008 | Wales et al. |
| 7,472,815 B2 | 1/2009 | Shelton, IV et al. |
| 7,479,148 B2 | 1/2009 | Beaupre |
| 7,479,160 B2 | 1/2009 | Branch et al. |
| 7,494,468 B2 | 2/2009 | Rabiner et al. |
| 7,503,893 B2 | 3/2009 | Kucklick |
| 7,506,790 B2 | 3/2009 | Shelton, IV |
| 7,506,791 B2 | 3/2009 | Omaits et al. |
| 7,524,320 B2 | 4/2009 | Tierney et al. |
| 7,534,243 B1 | 5/2009 | Chin et al. |

(56) References Cited

U.S. PATENT DOCUMENTS

| | | | |
|---|---|---|---|
| D594,983 S | 6/2009 | Price et al. |
| 7,549,564 B2 | 6/2009 | Boudreaux |
| 7,559,450 B2 | 7/2009 | Wales et al. |
| 7,567,012 B2 | 7/2009 | Namikawa |
| 7,654,431 B2 | 2/2010 | Hueil et al. |
| 7,665,647 B2 | 2/2010 | Shelton, IV et al. |
| 7,670,334 B2 | 3/2010 | Hueil et al. |
| 7,674,263 B2 | 3/2010 | Ryan |
| 7,691,098 B2 | 4/2010 | Wallace et al. |
| 7,713,202 B2 | 5/2010 | Boukhny et al. |
| 7,714,481 B2 | 5/2010 | Sakai |
| D618,797 S | 6/2010 | Price et al. |
| 7,751,115 B2 | 7/2010 | Song |
| 7,770,774 B2 | 8/2010 | Mastri et al. |
| 7,770,775 B2 | 8/2010 | Shelton, IV et al. |
| 7,780,054 B2 | 8/2010 | Wales |
| 7,780,659 B2 | 8/2010 | Okada et al. |
| 7,784,662 B2 | 8/2010 | Wales et al. |
| 7,798,386 B2 | 9/2010 | Schall et al. |
| 7,806,891 B2 | 10/2010 | Nowlin et al. |
| 7,810,693 B2 | 10/2010 | Broehl et al. |
| 7,824,401 B2 | 11/2010 | Manzo et al. |
| 7,854,735 B2 | 12/2010 | Houser et al. |
| D631,155 S | 1/2011 | Peine et al. |
| 7,861,906 B2 | 1/2011 | Doll et al. |
| 7,876,030 B2 | 1/2011 | Taki et al. |
| D631,965 S | 2/2011 | Price et al. |
| 7,905,881 B2 | 3/2011 | Masuda et al. |
| 7,959,050 B2 | 6/2011 | Smith et al. |
| 7,959,626 B2 | 6/2011 | Hong et al. |
| 8,038,693 B2 | 10/2011 | Allen |
| 8,061,014 B2 | 11/2011 | Smith et al. |
| 8,089,197 B2 | 1/2012 | Rinner et al. |
| 8,157,145 B2 | 4/2012 | Shelton, IV et al. |
| 8,177,800 B2 | 5/2012 | Spitz et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,253,303 B2 | 8/2012 | Giordano et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0077550 A1 | 6/2002 | Rabiner et al. |
| 2002/0156493 A1 | 10/2002 | Houser et al. |
| 2003/0055443 A1 | 3/2003 | Spotnitz |
| 2003/0204199 A1 | 10/2003 | Novak et al. |
| 2003/0212332 A1 | 11/2003 | Fenton et al. |
| 2003/0212422 A1 | 11/2003 | Fenton et al. |
| 2004/0030254 A1 | 2/2004 | Babaev |
| 2004/0047485 A1 | 3/2004 | Sherrit et al. |
| 2004/0054364 A1 | 3/2004 | Aranyi et al. |
| 2004/0092921 A1 | 5/2004 | Kadziauskas et al. |
| 2004/0097919 A1 | 5/2004 | Wellman et al. |
| 2004/0097996 A1 | 5/2004 | Rabiner et al. |
| 2004/0199193 A1* | 10/2004 | Hayashi et al. ............... 606/169 |
| 2004/0204728 A1 | 10/2004 | Haefner |
| 2004/0243157 A1 | 12/2004 | Connor et al. |
| 2004/0260300 A1 | 12/2004 | Gorensek et al. |
| 2005/0033337 A1 | 2/2005 | Muir et al. |
| 2005/0049546 A1 | 3/2005 | Messerly et al. |
| 2005/0143769 A1 | 6/2005 | White et al. |
| 2005/0149108 A1 | 7/2005 | Cox |
| 2005/0165345 A1* | 7/2005 | Laufer et al. ................... 604/26 |
| 2005/0177184 A1 | 8/2005 | Easley |
| 2005/0192610 A1 | 9/2005 | Houser et al. |
| 2005/0209620 A1 | 9/2005 | Du et al. |
| 2005/0261581 A1 | 11/2005 | Hughes et al. |
| 2005/0261588 A1 | 11/2005 | Makin et al. |
| 2005/0288659 A1 | 12/2005 | Kimura et al. |
| 2006/0019114 A1* | 1/2006 | Thies et al. ................... 428/522 |
| 2006/0030797 A1 | 2/2006 | Zhou et al. |
| 2006/0063130 A1 | 3/2006 | Hayman et al. |
| 2006/0079878 A1 | 4/2006 | Houser |
| 2006/0084963 A1 | 4/2006 | Messerly |
| 2006/0116675 A1* | 6/2006 | McClurken et al. ............ 606/51 |
| 2006/0190034 A1 | 8/2006 | Nishizawa et al. |
| 2006/0211943 A1 | 9/2006 | Beaupre |
| 2006/0235306 A1 | 10/2006 | Cotter et al. |
| 2006/0253050 A1 | 11/2006 | Yoshimine et al. |
| 2007/0016235 A1 | 1/2007 | Tanaka et al. |
| 2007/0016236 A1 | 1/2007 | Beaupre |
| 2007/0038157 A1* | 2/2007 | Yamada et al. .................. 601/2 |
| 2007/0055228 A1 | 3/2007 | Berg et al. |
| 2007/0060915 A1 | 3/2007 | Kucklick |
| 2007/0060935 A1 | 3/2007 | Schwardt et al. |
| 2007/0063618 A1 | 3/2007 | Bromfield |
| 2007/0106317 A1 | 5/2007 | Shelton, IV et al. |
| 2007/0129716 A1 | 6/2007 | Daw et al. |
| 2007/0130771 A1 | 6/2007 | Ehlert et al. |
| 2007/0131034 A1 | 6/2007 | Ehlert et al. |
| 2007/0149881 A1 | 6/2007 | Rabin |
| 2007/0162050 A1 | 7/2007 | Sartor |
| 2007/0173872 A1 | 7/2007 | Neuenfeldt |
| 2007/0185380 A1 | 8/2007 | Kucklick |
| 2007/0219481 A1 | 9/2007 | Babaev |
| 2007/0239028 A1 | 10/2007 | Houser et al. |
| 2007/0249941 A1 | 10/2007 | Salehi et al. |
| 2007/0260234 A1 | 11/2007 | McCullagh et al. |
| 2007/0265560 A1* | 11/2007 | Soltani et al. .................. 604/22 |
| 2007/0275348 A1 | 11/2007 | Lemon |
| 2007/0282335 A1 | 12/2007 | Young et al. |
| 2007/0287933 A1 | 12/2007 | Phan et al. |
| 2008/0009848 A1 | 1/2008 | Paraschiv et al. |
| 2008/0058585 A1 | 3/2008 | Novak et al. |
| 2008/0058775 A1 | 3/2008 | Darian et al. |
| 2008/0058845 A1 | 3/2008 | Shimizu et al. |
| 2008/0082039 A1 | 4/2008 | Babaev |
| 2008/0082098 A1 | 4/2008 | Tanaka et al. |
| 2008/0172051 A1 | 7/2008 | Masuda et al. |
| 2008/0177268 A1 | 7/2008 | Daum et al. |
| 2008/0188878 A1 | 8/2008 | Young |
| 2008/0200940 A1 | 8/2008 | Eichmann et al. |
| 2008/0208231 A1 | 8/2008 | Ota et al. |
| 2008/0234708 A1 | 9/2008 | Houser et al. |
| 2008/0234709 A1 | 9/2008 | Houser |
| 2008/0234710 A1 | 9/2008 | Neurohr et al. |
| 2008/0234711 A1 | 9/2008 | Houser et al. |
| 2008/0243106 A1 | 10/2008 | Coe et al. |
| 2008/0245371 A1 | 10/2008 | Gruber |
| 2008/0249553 A1 | 10/2008 | Gruber et al. |
| 2008/0262490 A1 | 10/2008 | Williams |
| 2008/0281200 A1 | 11/2008 | Voic et al. |
| 2008/0287948 A1 | 11/2008 | Newton et al. |
| 2009/0030311 A1 | 1/2009 | Stulen et al. |
| 2009/0030351 A1 | 1/2009 | Wiener et al. |
| 2009/0030437 A1 | 1/2009 | Houser et al. |
| 2009/0030438 A1 | 1/2009 | Stulen |
| 2009/0036911 A1 | 2/2009 | Stulen |
| 2009/0036912 A1 | 2/2009 | Wiener et al. |
| 2009/0036913 A1 | 2/2009 | Wiener et al. |
| 2009/0036914 A1 | 2/2009 | Houser |
| 2009/0054886 A1 | 2/2009 | Yachi et al. |
| 2009/0054894 A1 | 2/2009 | Yachi |
| 2009/0076506 A1 | 3/2009 | Baker |
| 2009/0082716 A1 | 3/2009 | Akahoshi |
| 2009/0105750 A1 | 4/2009 | Price et al. |
| 2009/0118802 A1 | 5/2009 | Mioduski et al. |
| 2009/0138006 A1 | 5/2009 | Bales et al. |
| 2009/0143795 A1 | 6/2009 | Robertson |
| 2009/0143796 A1 | 6/2009 | Stulen et al. |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0143806 A1 | 6/2009 | Witt et al. |

(56) References Cited

U.S. PATENT DOCUMENTS

| | | |
|---|---|---|
| 2009/0270853 A1 | 10/2009 | Yachi et al. |
| 2009/0318945 A1 | 12/2009 | Yoshimine et al. |
| 2009/0327715 A1 | 12/2009 | Smith et al. |
| 2010/0004668 A1 | 1/2010 | Smith et al. |
| 2010/0004669 A1 | 1/2010 | Smith et al. |
| 2010/0016785 A1 | 1/2010 | Takuma |
| 2010/0030248 A1 | 2/2010 | Palmer et al. |
| 2010/0036370 A1 | 2/2010 | Mirel et al. |
| 2010/0036405 A1 | 2/2010 | Giordano et al. |
| 2010/0069940 A1 | 3/2010 | Miller et al. |
| 2010/0158307 A1 | 6/2010 | Kubota et al. |
| 2010/0179577 A1 | 7/2010 | Houser |
| 2010/0187283 A1 | 7/2010 | Crainich et al. |
| 2010/0193567 A1 | 8/2010 | Scheib et al. |
| 2010/0298743 A1 | 11/2010 | Nield et al. |
| 2010/0298851 A1 | 11/2010 | Nield |
| 2010/0331869 A1 | 12/2010 | Voegele et al. |
| 2010/0331870 A1 | 12/2010 | Wan et al. |
| 2010/0331871 A1 | 12/2010 | Nield et al. |
| 2010/0331872 A1 | 12/2010 | Houser et al. |
| 2011/0009850 A1 | 1/2011 | Main et al. |
| 2011/0015627 A1 | 1/2011 | DiNardo et al. |
| 2011/0015631 A1 | 1/2011 | Wiener et al. |
| 2011/0015660 A1 | 1/2011 | Wiener et al. |
| 2011/0082486 A1 | 4/2011 | Messerly et al. |
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087218 A1 | 4/2011 | Boudreaux et al. |
| 2011/0087256 A1 | 4/2011 | Wiener et al. |
| 2011/0125175 A1 | 5/2011 | Stulen et al. |
| 2011/0196286 A1 | 8/2011 | Robertson et al. |
| 2011/0196287 A1 | 8/2011 | Robertson et al. |
| 2011/0196398 A1 | 8/2011 | Robertson et al. |
| 2011/0196399 A1 | 8/2011 | Robertson et al. |
| 2011/0196400 A1 | 8/2011 | Robertson et al. |
| 2011/0196401 A1 | 8/2011 | Robertson et al. |
| 2011/0196402 A1 | 8/2011 | Robertson et al. |
| 2011/0196403 A1 | 8/2011 | Robertson et al. |
| 2011/0196404 A1 | 8/2011 | Dietz et al. |
| 2011/0196405 A1 | 8/2011 | Dietz |
| 2011/0288452 A1 | 11/2011 | Houser et al. |
| 2012/0029546 A1 | 2/2012 | Robertson |
| 2012/0059289 A1 | 3/2012 | Nield et al. |
| 2012/0078139 A1 | 3/2012 | Aldridge et al. |
| 2012/0078247 A1 | 3/2012 | Worrell et al. |
| 2012/0083783 A1 | 4/2012 | Davison et al. |
| 2012/0083784 A1 | 4/2012 | Davison et al. |
| 2012/0184946 A1 | 7/2012 | Price et al. |
| 2012/0203257 A1 | 8/2012 | Stulen et al. |

FOREIGN PATENT DOCUMENTS

| | | |
|---|---|---|
| CN | 1694649 A | 11/2005 |
| CN | 1922563 A | 2/2007 |
| CN | 101040799 A | 9/2007 |
| EP | 0171967 A2 | 2/1986 |
| EP | 0443256 A1 | 8/1991 |
| EP | 0456470 A1 | 11/1991 |
| EP | 0482195 B1 | 4/1992 |
| EP | 0482195 B1 | 1/1996 |
| EP | 0612570 B1 | 6/1997 |
| EP | 0908148 B1 | 1/2002 |
| EP | 0908155 B1 | 6/2003 |
| EP | 1199044 B1 | 12/2005 |
| EP | 1433425 B1 | 6/2006 |
| EP | 1844720 A1 | 10/2007 |
| EP | 1862133 A1 | 12/2007 |
| EP | 1974771 A1 | 10/2008 |
| EP | 1832259 B1 | 6/2009 |
| EP | 2074959 A1 | 7/2009 |
| GB | 2032221 A | 4/1980 |
| GB | 2447767 B | 8/2011 |
| JP | 6-104503 A | 4/1994 |
| JP | 8-24266 A | 1/1996 |
| JP | 10-295700 A | 11/1998 |
| JP | 2005027026 A | 1/2005 |
| JP | 2006217716 A | 8/2006 |
| WO | WO 92/22259 A2 | 12/1992 |
| WO | WO 93/14708 A1 | 8/1993 |
| WO | WO 98/37815 A1 | 9/1998 |
| WO | WO 01/54590 A1 | 8/2001 |
| WO | WO 2005/122917 A1 | 12/2005 |
| WO | WO 2006/042210 A2 | 4/2006 |
| WO | WO 2006/058223 A2 | 6/2006 |
| WO | WO 2006/129465 A1 | 12/2006 |
| WO | WO 2007/008710 A2 | 1/2007 |
| WO | WO 2007/047531 A2 | 4/2007 |
| WO | WO 2007/143665 A2 | 12/2007 |
| WO | WO 2008/016886 A2 | 2/2008 |
| WO | WO 2008/130793 A1 | 10/2008 |
| WO | WO 2009/018406 A2 | 2/2009 |
| WO | WO 2009/027065 | 3/2009 |
| WO | WO 2011/144911 A1 | 11/2011 |

OTHER PUBLICATIONS

U.S. Appl. No. 11/881,636, filed Jul. 27, 2007.
International Search Report for PCT/US2008/070983, Nov. 7, 2008 (5 pages).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
U.S. Appl. No. 12/181,816, filed Jul. 29, 2008.
U.S. Appl. No. 11/881,602, filed Jul. 27, 2007.
U.S. Appl. No. 11/888,081, filed Jul. 31, 2007.
U.S. Appl. No. 11/881,654, filed Jul. 27, 2007.
U.S. Appl. No. 11/888,171, filed Jul. 31, 2007.
U.S. Appl. No. 11/998,758, filed Nov. 30, 2007.
U.S. Appl. No. 11/881,662, filed Jul. 27, 2007.
U.S. Appl. No. 11/888,222, filed Jul. 31, 2007.
U.S. Appl. No. 12/245,158, filed Oct. 3, 2008.
U.S. Appl. No. 29/292,295, filed Oct. 5, 2007.
U.S. Appl. No. 11/998,543, filed Nov. 30, 2007.
U.S. Appl. No. 29/327,737, filed Nov. 12, 2008.
U.S. Appl. No. 12/274,884, filed Nov. 20, 2008.
Technology Overview, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Lim et al., "A Review of Mechanism Used in Laparoscopic Surgical Instruments," Mechanism and Machine Theory, vol. 38, pp. 1133-1147, (2003).
U.S. Appl. No. 12/469,293, filed May 20, 2009.
U.S. Appl. No. 12/469,308, filed May 20, 2009.
AST Products, Inc., "Principles of Video Contact Angle Analysis," 20 pages, (2006).
U.S. Appl. No. 12/503,769, filed Jul. 15, 2009.
U.S. Appl. No. 12/503,770, filed Jul. 15, 2009.
U.S. Appl. No. 12/503,766, filed Jul. 15, 2009.
U.S. Appl. No. 12/490,906, filed Jun. 24, 2009.
U.S. Appl. No. 12/490,922, filed Jun. 24, 2009.
U.S. Appl. No. 12/490,933, filed Jun. 24, 2009.
U.S. Appl. No. 12/490,948, filed Jun. 24, 2009.
U.S. Appl. No. 12/703,860, filed Feb. 11, 2010.
U.S. Appl. No. 12/703,864, filed Feb. 11, 2010.
U.S. Appl. No. 12/703,866, filed Feb. 11, 2010.
U.S. Appl. No. 12/703,870, filed Feb. 11, 2010.
U.S. Appl. No. 12/703,875, filed Feb. 11, 2010.
U.S. Appl. No. 12/703,877, filed Feb. 11, 2010.
U.S. Appl. No. 12/703,879, filed Feb. 11, 2010.
U.S. Appl. No. 12/703,885, filed Feb. 11, 2010.
U.S. Appl. No. 12/703,893, filed Feb. 11, 2010.

(56) References Cited

OTHER PUBLICATIONS

U.S. Appl. No. 12/703,899, filed Feb. 11, 2010.
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Incropera et al., Fundamentals of Heat and Mass Transfer, Wiley, New York (1990). (Book—not attached).
F. A. Duck, "Optical Properties of Tissue Including Ultraviolet and Infrared Radiation," pp. 43-71 in *Physical Properties of Tissue* (1990).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Campbell et al, "Thermal Imaging in Surgery," p. 19-3, in *Medical Infrared Imaging*, N. A. Diakides and J. D. Bronzino, Eds. (2008).
U.S. Appl. No. 12/896,351, filed Oct. 1, 2010.
U.S. Appl. No. 12/896,411, filed Oct. 1, 2010.
U.S. Appl. No. 12/896,420, filed Oct. 1, 2010.
U.S. Appl. No. 29/402,697, filed Sep. 26, 2011.
U.S. Appl. No. 29/402,699, filed Sep. 26, 2011.
U.S. Appl. No. 29/402,700, filed Sep. 26, 2011.
U.S. Appl. No. 29/402,701, filed Sep. 26, 2011.
U.S. Appl. No. 13/251,766, filed Oct. 3, 2011.
U.S. Appl. No. 29/404,676, filed Oct. 24, 2011.
U.S. Appl. No. 13/296,829, filed Nov. 15, 2011.
U.S. Appl. No. 13/448,175, filed Apr. 16, 2012.
U.S. Appl. No. 13/151,181, filed Jun. 2, 2011.
U.S. Appl. No. 13/369,561, filed Feb. 9, 2012.
U.S. Appl. No. 13/369,569, filed Feb. 9, 2012.
U.S. Appl. No. 13/369,578, filed Feb. 9, 2012.
U.S. Appl. No. 13/369,584, filed Feb. 9, 2012.
U.S. Appl. No. 13/369,588, filed Feb. 9, 2012.
U.S. Appl. No. 13/369,594, filed Feb. 9, 2012.
U.S. Appl. No. 13/369,601, filed Feb. 9, 2012.
U.S. Appl. No. 13/369,609, filed Feb. 9, 2012.
U.S. Appl. No. 13/369,629, filed Feb. 9, 2012.
U.S. Appl. No. 13/369,666, filed Feb. 9, 2012.
U.S. Appl. No. 13/545,292, filed Jul. 10, 2012.
U.S. Appl. No. 13/584,020, filed Aug. 13, 2012.
U.S. Appl. No. 13/584,445, filed Aug. 13, 2012.
U.S. Appl. No. 13/584,878, filed Aug. 14, 2012.
U.S. Appl. No. 13/585,124, filed Aug. 14, 2012.
U.S. Appl. No. 13/585,292, filed Aug. 14, 2012.

* cited by examiner

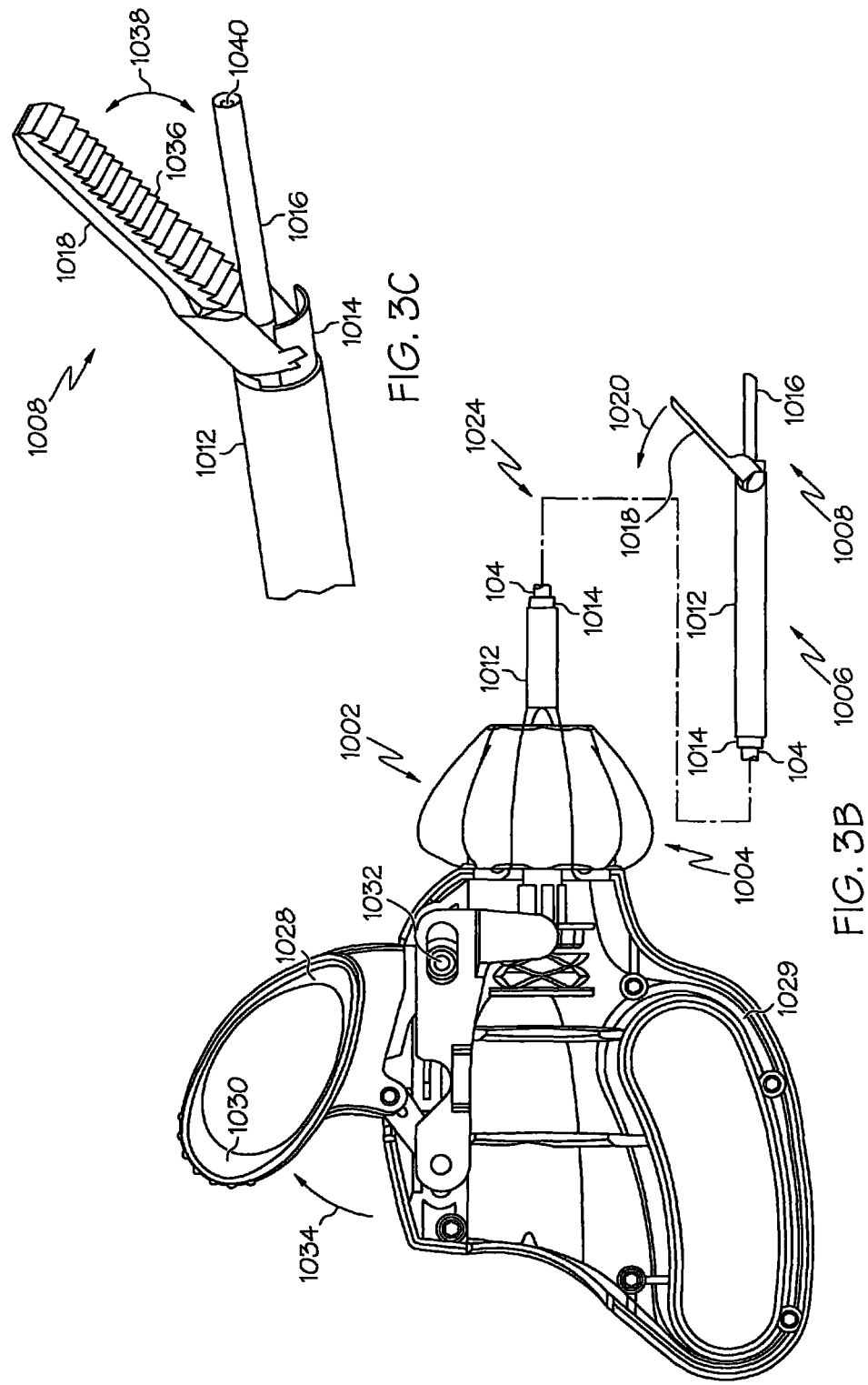

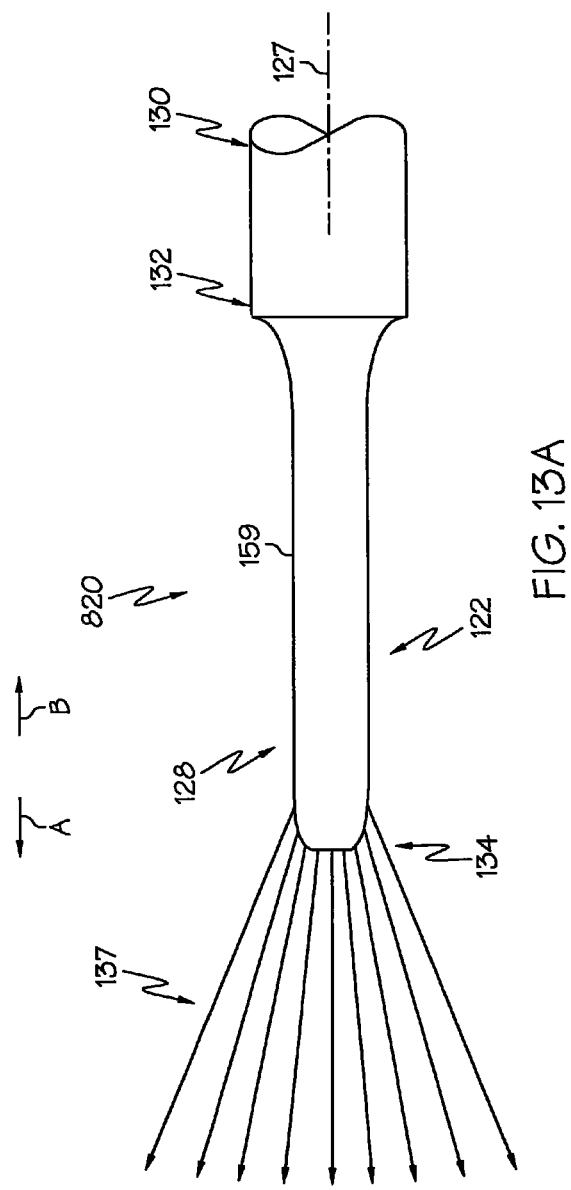

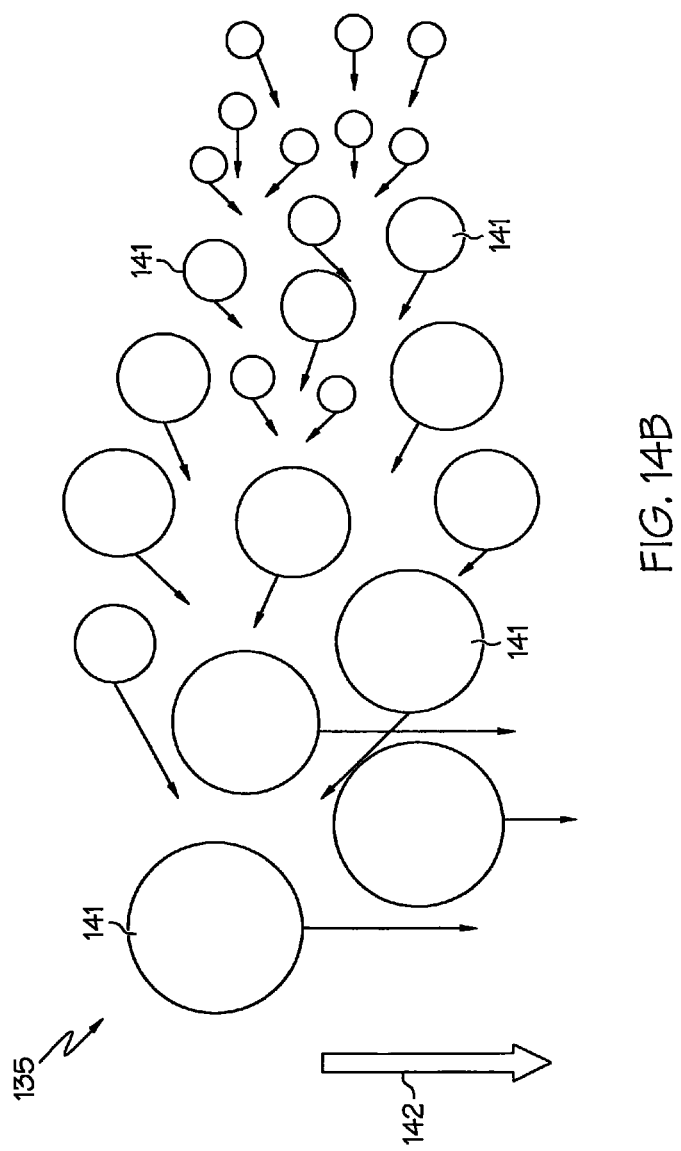

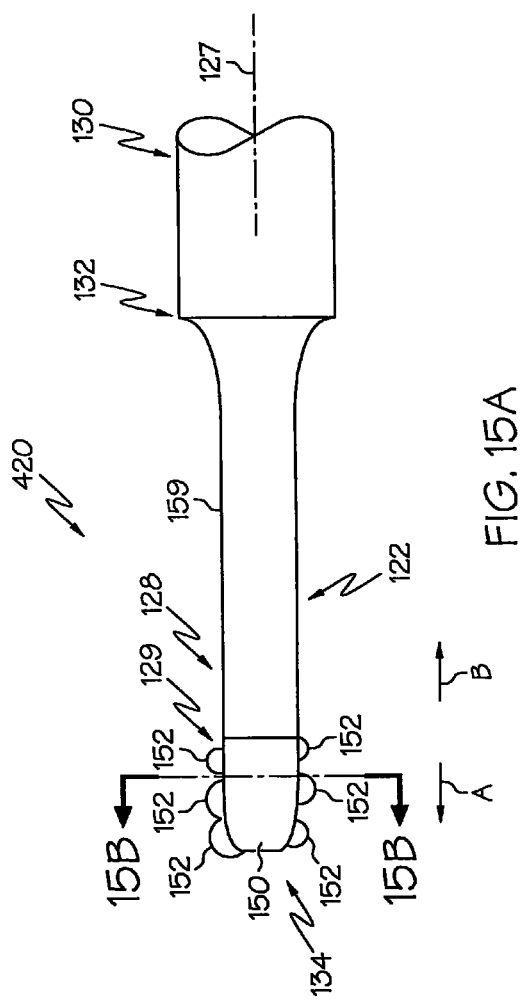
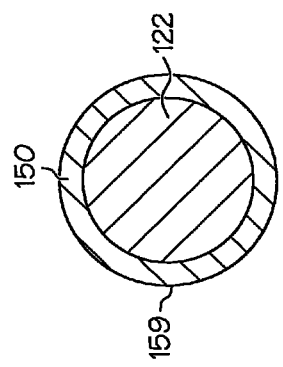
FIG. 15A
FIG. 15B

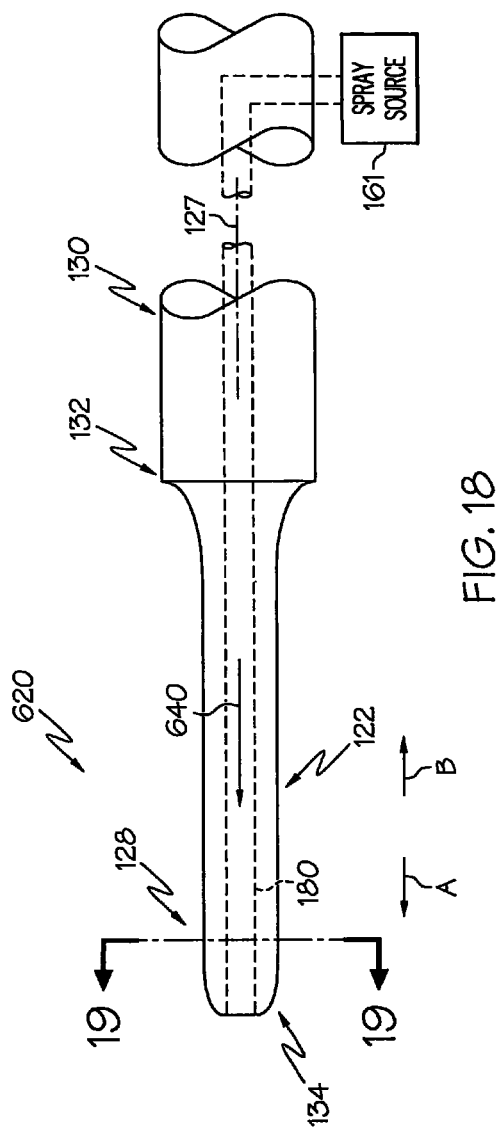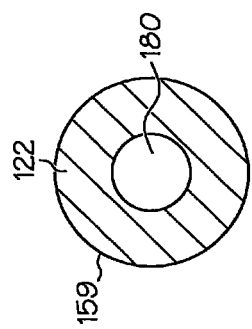

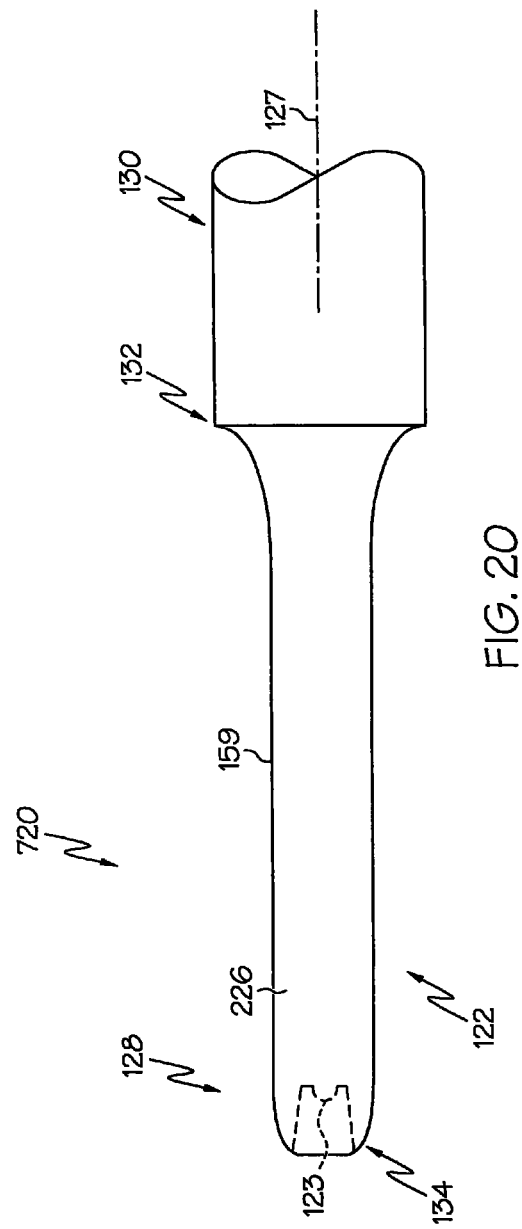

ULTRASONIC SURGICAL INSTRUMENTS

BACKGROUND

The subject application is related a co-pending and commonly-owned application filed on even date herewith, the disclosure of which is hereby incorporated by reference in its entirety, the application being respectively entitled Ultrasonic Surgical Instruments to Foster B. Stulen, application Ser. No. 11/881,636, now U.S. Patent Application Publication No. 2009/0030438.

Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate tissue using energy in the form of mechanical vibrations transmitted to a surgical end effector at ultrasonic frequencies. Ultrasonic vibrations, when transmitted to organic tissue at suitable energy levels and using a suitable end effector, may be used to cut, dissect, or coagulate tissue or elevate or separate muscle tissue off bone. Ultrasonic instruments utilizing solid core technology are particularly advantageous because of the amount of ultrasonic energy that may be transmitted from the ultrasonic transducer, through an ultrasonic transmission waveguide, to the surgical end effector. Such instruments may be used for open procedures or minimally invasive procedures, such as endoscopic or laparoscopic procedures, wherein the end effector is passed through a trocar to reach the surgical site.

Activating or exciting the single or multiple element end effector (e.g., cutting blade, ball coagulator) of such instruments at ultrasonic frequencies induces longitudinal, transverse, or torsional vibratory movement that generates localized heat within adjacent tissue, facilitating both cutting and coagulating. Because of the nature of ultrasonic instruments, a particular ultrasonically actuated end effector may be designed to perform numerous functions, including, for example, cutting and coagulating.

Ultrasonic vibration is induced in the surgical end effector by electrically exciting a transducer, for example. The transducer may be constructed of one or more piezoelectric or magnetostrictive elements in the instrument hand piece. Vibrations generated by the transducer section are transmitted to the surgical end effector via an ultrasonic waveguide extending from the transducer section to the surgical end effector. The waveguides and end effectors are most preferably designed to resonate at the same frequency as the transducer. When an end effector is attached to a transducer the overall system frequency may be the same frequency as the transducer itself.

The transducer and the end effector may be designed to resonate at two different frequencies and when joined or coupled may resonate at a third frequency. The zero-to-peak amplitude of the longitudinal ultrasonic vibration at the tip, d, of the end effector behaves as a simple sinusoid at the resonant frequency as given by:

$$d = A \sin(\omega t)$$

where:
$\omega$=the radian frequency which equals $2\pi$ times the cyclic frequency, f; and
A=the zero-to-peak amplitude.
The longitudinal excursion is defined as the peak-to-peak (p-t-p) amplitude, which is just twice the amplitude of the sine wave or 2 A.

Solid core ultrasonic surgical instruments may be divided into two types, single element end effector devices and multiple-element end effectors. Single element end effector devices include instruments such as scalpels (e.g., blades, sharp hook blades, dissecting hook blades, curved blades) and ball coagulators. Single-element end effector instruments have limited ability to apply blade-to-tissue pressure when the tissue is soft and loosely supported. Substantial pressure may be necessary to effectively couple ultrasonic energy to the tissue. The inability of a single-element end effector to grasp the tissue results in a further inability to fully coapt tissue surfaces while applying ultrasonic energy, leading to less-than-desired hemostasis and tissue joining. The use of multiple-element end effectors such as clamping coagulators includes a mechanism to press tissue against an ultrasonic blade that can overcome these deficiencies.

Ultrasonic clamp coagulators or clamped coagulating shears provide an improved ultrasonic surgical instrument for cutting/coagulating tissue, particularly loose and unsupported tissue, wherein the ultrasonic blade is employed in conjunction with a clamp for applying a compressive or biasing force to the tissue, whereby faster coagulation and cutting of the tissue.

As the distal end of the end effector, or more particularly, the blade, cuts through or coagulates tissue it comes into contact with fluid (e.g., blood, tissue particles). When the distal end of the blade contacts this fluid, a fine mist in the form of a diverging plume of fluid particles may emanate from the distal end of the blade. This plume of mist may limit visibility at the surgical site. It would be desirable to provide an ultrasonic instrument which reduces the plume of mist emanating from the distal end of the end effector.

SUMMARY

In one general aspect, the various embodiments are directed to a surgical instrument with mist reducing features. The surgical instrument may comprise a transducer configured to produce vibrations at a predetermined frequency. An ultrasonic blade extends along a longitudinal axis and is coupled to the transducer. The ultrasonic blade comprises a body without a channel, and the body comprises a proximal end and a distal end. The distal end is movable relative to the longitudinal axis by the vibrations produced by the transducer. At least a portion of the body comprises at least one layer of a first material to globalize fluid particles in contact therewith.

In other embodiments, the body may also comprise additional elements which may lead to the reduction of mist. In one embodiment, the body may comprise at least one layer of a first material which comprises a material suitable to carry an electrical charge. In another embodiment, the body may comprise a longitudinally extending bore formed within the blade.

FIGURES

The novel features of the various embodiments are set forth with particularity in the appended claims. The various embodiments, however, both as to organization and methods of operation, may best be understood by reference to the following description, taken in conjunction with the accompanying drawings as follows.

FIG. 3B illustrates one embodiment of a clamp coagulator comprising a multi-element end effector as shown in FIG. 1B.

FIG. 3C illustrates a perspective view of the multi-element end effector as shown in FIGS. 1B and 3B.

FIG. 4 is a side view of one embodiment of an ultrasonic blade;

FIG. 5 is a cross-sectional view of the ultrasonic blade taken along line 5-5 in FIG. 4; and FIG. 6 is a perspective view of the ultrasonic blade shown in FIG. 4.

FIG. 7 is a side view of one embodiment of an ultrasonic blade;

FIG. 8 is a cross-sectional view of the ultrasonic blade taken along line 8-8 in FIG. 7; and FIG. 9 is a perspective view of the ultrasonic blade shown in FIG. 7.

FIG. 10 is a side view of one embodiment of an ultrasonic blade;

FIG. 11 is a cross-sectional view of the ultrasonic blade taken along line 11-11 in FIG. 10; and FIG. 12 is a perspective view of the ultrasonic blade shown in FIG. 10.

Figure 13B:
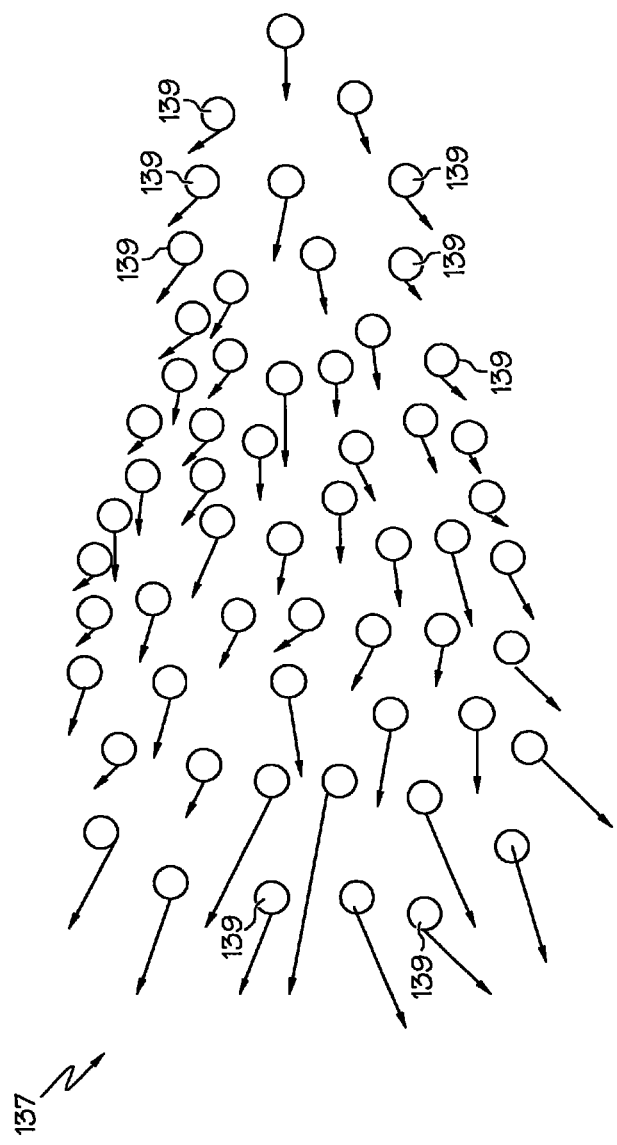

FIGS. 13A-B illustrate various embodiments of an ultrasonic blade, where:

FIG. 13A is a side view of an ultrasonic blade with a convex blade tip depicting a divergent plume mist; and FIG. 13B is a detail view of the divergent jet of fluid mist.

Figure 14A:
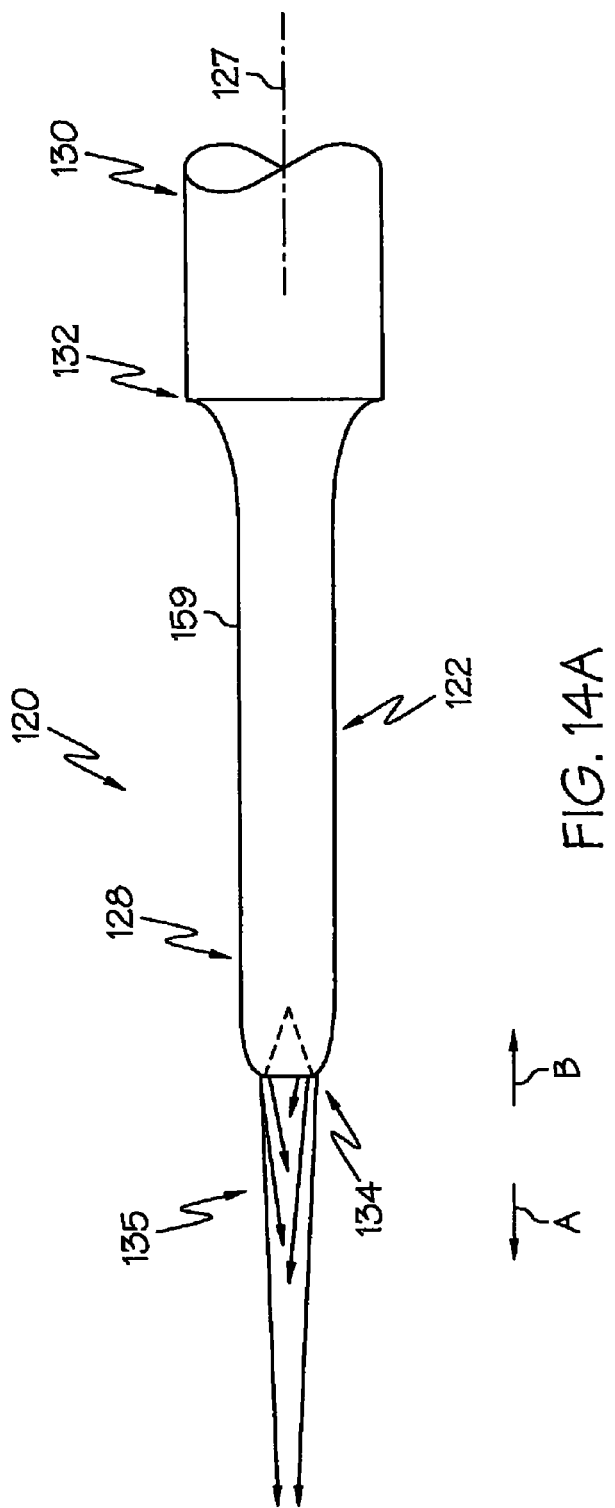

FIGS. 14A-B illustrate various embodiments of an ultrasonic blade, where:

FIG. 14A is a side view of an ultrasonic blade with a tapered concave surface formed at a distal end of the blade depicting a convergence of the fluid leaving the blade tip; and FIG. 14B is a detail view of the convergent jet of fluid mist.

FIGS. 15A-D illustrate various embodiments of an ultrasonic blade, where:

FIG. 15A is a side view of an ultrasonic blade with at least a portion of the ultrasonic blade coated with at least one layer of a material which may allow the fluid to form globules on the surface of the material; and FIG. 15B is cross-sectional view of the ultrasonic blade taken along line B-B in FIG. 15A.

Figure 15C:
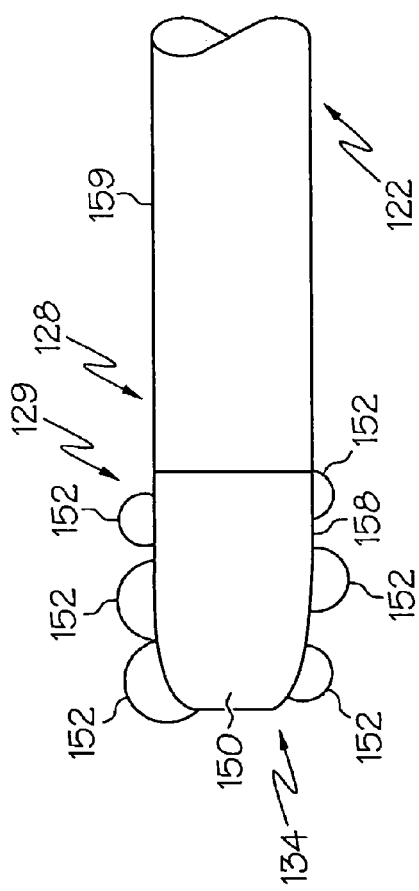

FIG. 15C is a detailed view of the ultrasonic blade of FIG. 15A.

Figure 15D:
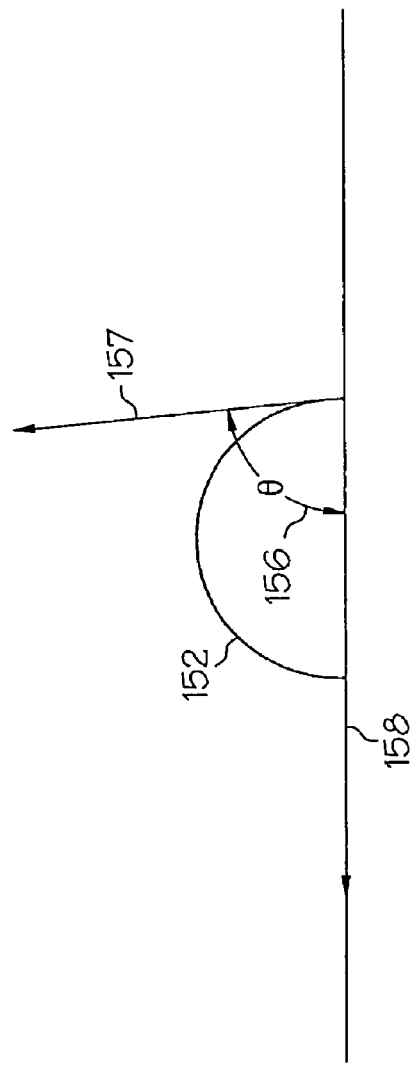

FIG. 15D illustrates a contact angle between a droplet and the surface of the ultrasonic blade of FIG. 15A.

Figure 16:
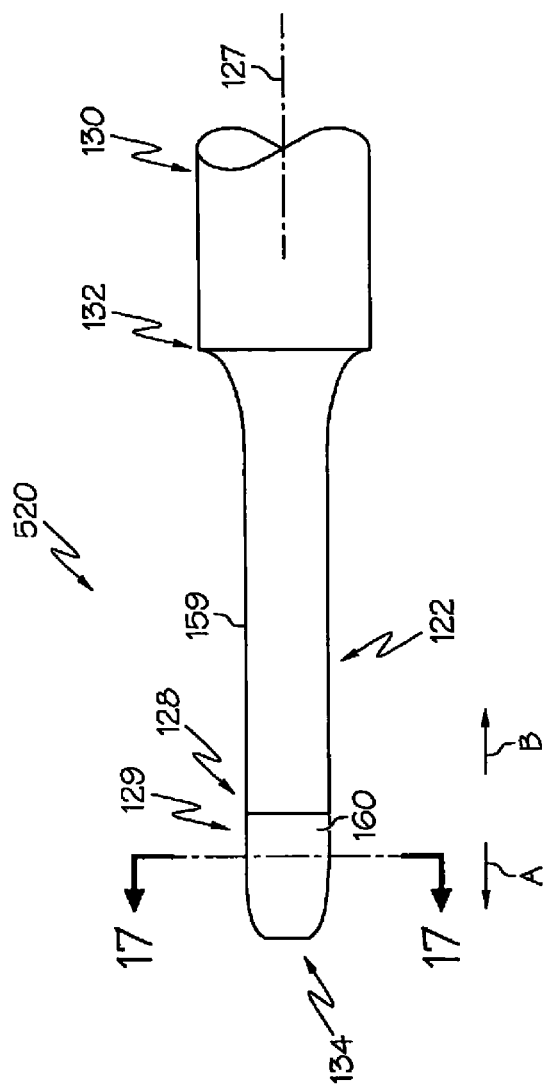
Figure 17:
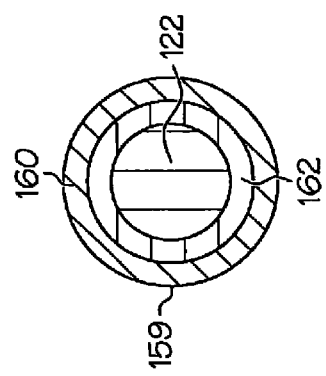

FIGS. 16-17 illustrate various embodiments of an ultrasonic blade, where:

FIG. 16 is a side view of an ultrasonic blade with portions of the blade coated with more than one material to provide an electric charge to the blade tip; and FIG. 17 is cross-sectional view of the ultrasonic blade taken along line 17-17 in FIG. 16.

FIGS. 18-19 illustrate various embodiments of an ultrasonic blade, where:

FIG. 18 is a side view of an ultrasonic blade with a longitudinally extending bore; and FIG. 19 is cross-sectional view of the ultrasonic blade taken along line 19-19 in FIG. 18.

FIG. 20 is a side view of an ultrasonic blade with a convex portion within a tapered concave surface thereof.

Figure 21:
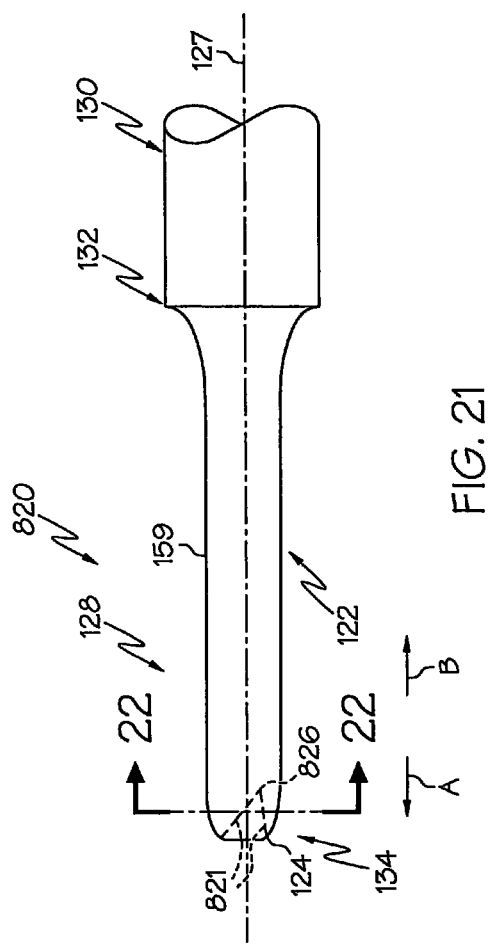
Figure 22:
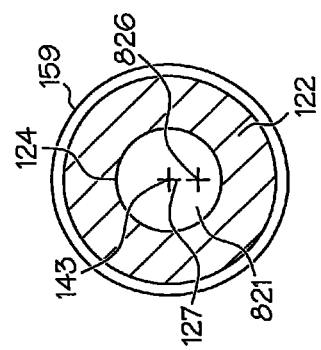

FIG. 21-22 illustrate various embodiments of an ultrasonic blade, where:

FIG. 21 is a side view of an ultrasonic blade with a tapered concave surface extending into the blade body asymmetrically.

FIG. 22 is a cross-sectional view of the ultrasonic blade taken along line 22-22 in FIG. 21.

Figure 23:
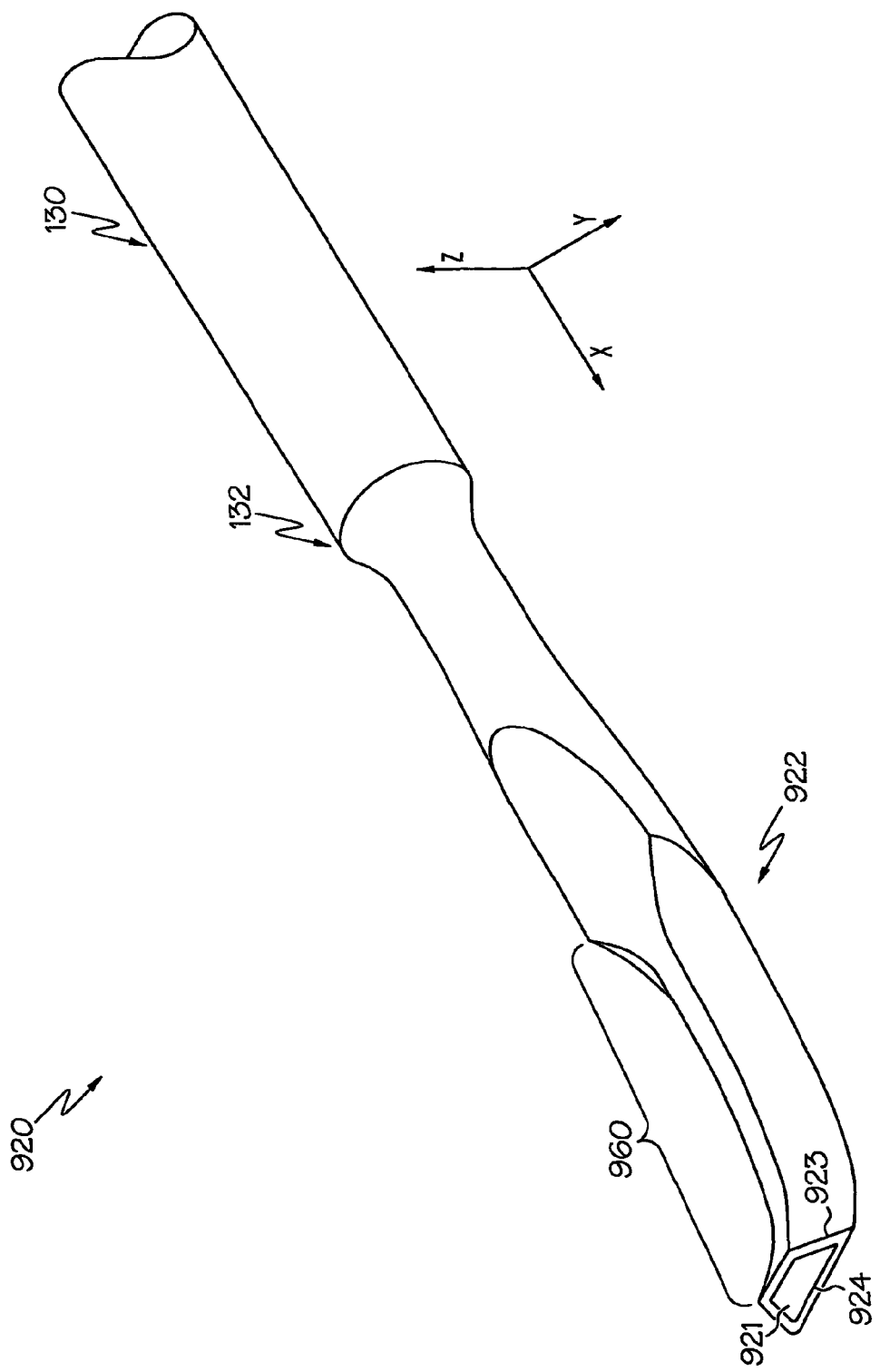

FIG. 23 is a perspective view of an asymmetric ultrasonic blade comprising a tapered concave surface extending inwardly into the blade body.

DESCRIPTION

Before explaining the various embodiments in detail, it should be noted that the embodiments are not limited in its application or use to the details of construction and arrangement of parts illustrated in the accompanying drawings and description. The illustrative embodiments may be implemented or incorporated in other embodiments, variations and modifications, and may be practiced or carried out in various ways. For example, the surgical instruments and blade configurations disclosed below are illustrative only and not meant to limit the scope or application thereof. Furthermore, unless otherwise indicated, the terms and expressions employed herein have been chosen for the purpose of describing the illustrative embodiments for the convenience of the reader and are not to limit the scope thereof.

The various embodiments relate, in general, to ultrasonic blades for use in surgical instruments and, more particularly, to ultrasonic blades comprising mist reducing features as described herein. The various embodiments relate, in general, to ultrasonic blades and instruments to improve visibility of the surgical site during surgery by reducing the mist plume created by fluid particles colliding with a distal end of an activated ultrasonic blade. Visibility of the surgical site may be improved through the mist reducing features of the ultrasonic blades which may comprise a tapered concave surface formed at the distal end of the blade, a tip coating, a lumen fluidically coupled to a spraying mechanism, a material to hold an electric charge, or any combination thereof. The term "tapered concave surface" is defined as a concave surface formed at a distal end of the blade that is tapered inwardly from its distal end to its proximal end in the direction indicated by arrow B, various embodiments of which are shown in FIGS. 4-23. A variety of different blade configurations are disclosed which may be useful for both open and laparoscopic applications.

Examples of ultrasonic surgical instruments are disclosed in U.S. Pat. Nos. 5,322,055 and 5,954,736 and in combination with ultrasonic blades and surgical instruments disclosed in U.S. Pat. Nos. 6,309,400 B2, 6,278,218 B1, 6,283,981 B1, and 6,325,811 B1, for example, are incorporated herein by reference in their entirety. These references disclose ultrasonic surgical instruments and blade configurations where a longitudinal mode of the blade is excited. Because of asymmetry or asymmetries, ultrasonic blades also may exhibit transverse and/or torsional motion where the characteristic "wavelength" of this non-longitudinal motion is generally less than that of the general longitudinal motion of the blade and its extender portion. Therefore, the wave shape of the non-longitudinal motion will present nodal positions of transverse/torsional motion along the tissue effector while the net motion of the active blade along its tissue effector is non-zero (i.e., will have at least longitudinal motion along the length extending from its distal end, an antinode of longitudinal motion, to the first nodal position of longitudinal motion that is proximal to the tissue effector portion).

Certain embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and that the scope of the various embodiments is defined solely by the claims. The features illustrated or described in connection with one embodiment may be combined with the features of other embodiments. Such modifications and variations are intended to be included within the scope of the claims.

Figure 1A:
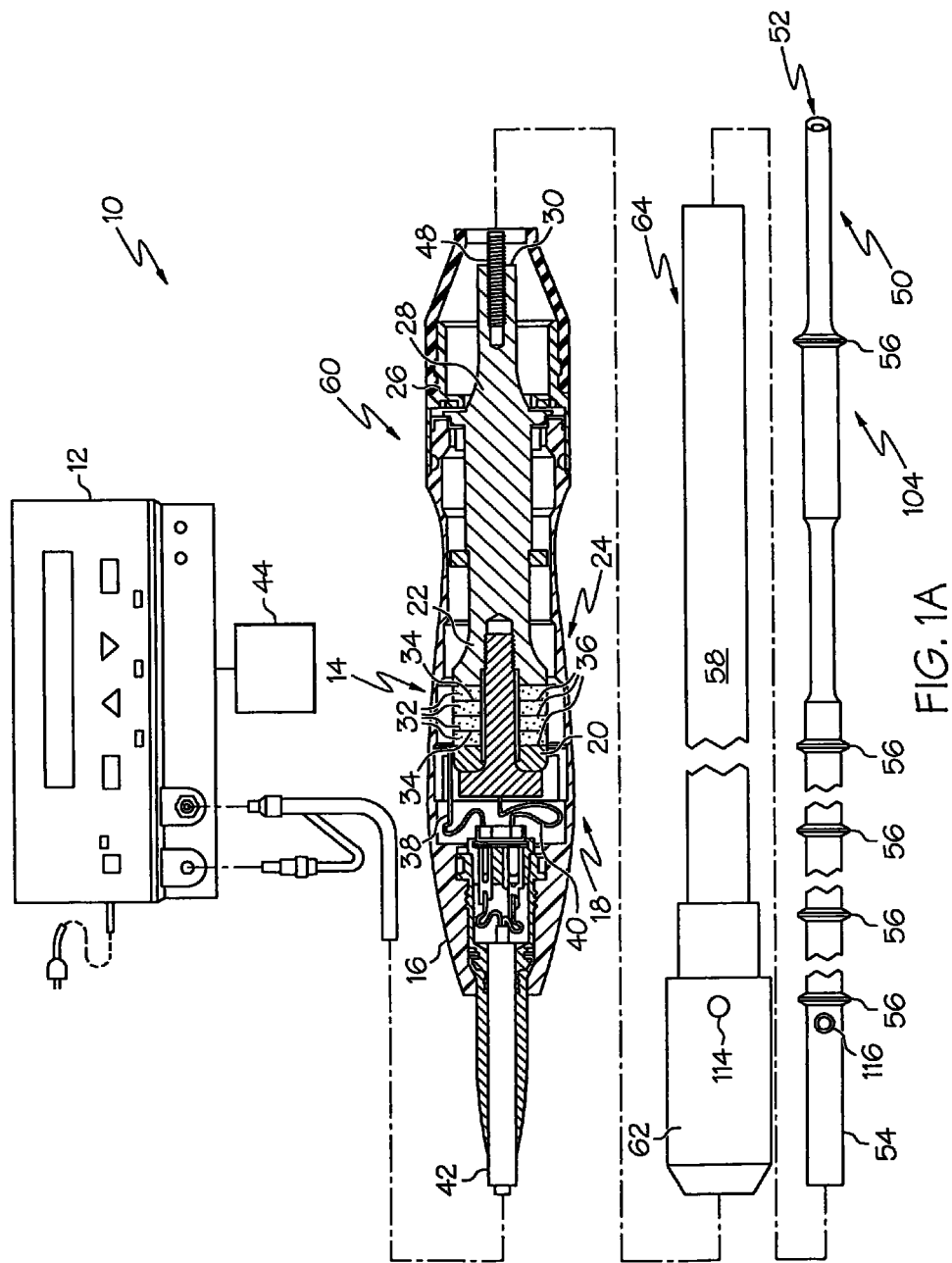
FIG. 1A illustrates one embodiment of an ultrasonic system comprising a single element end effector.

FIG. 1A illustrates one embodiment of an ultrasonic system 10 comprising a single element end effector. One embodiment of the ultrasonic system 10 comprises an ultrasonic signal generator 12 coupled to an ultrasonic transducer 14, a hand piece assembly 60 comprising a hand piece housing 16, and an ultrasonically actuatable single element end effector or ultrasonically actuatable blade 50. The ultrasonic transducer 14, which is known as a "Langevin stack", generally includes a transduction portion 18, a first resonator portion or end-bell 20, and a second resonator portion or fore-bell 22, and ancillary components. The total construction of these components is a resonator. The ultrasonic transducer 14 is preferably an integral number of one-half system wavelengths ($n\lambda/2$; where "n" is any positive integer; e.g., n=1, 2, 3 . . . ) in length as will be described in more detail later. An acoustic assembly 24 includes the ultrasonic transducer 14, a nose cone 26, a velocity transformer 28, and a surface 30.

It will be appreciated that the terms "proximal" and "distal" are used herein with reference to a clinician gripping the hand piece assembly 60. Thus, the blade 50 is distal with respect to the more proximal hand piece assembly 60. It will be further appreciated that, for convenience and clarity, spatial terms such as "top" and "bottom" also are used herein with respect to the clinician gripping the hand piece assembly 60. However, surgical instruments are used in many orientations and positions, and these terms are not intended to be limiting and absolute.

The distal end of the end-bell 20 is connected to the proximal end of the transduction portion 18, and the proximal end of the fore-bell 22 is connected to the distal end of the transduction portion 18. The fore-bell 22 and the end-bell 20 have a length determined by a number of variables, including the thickness of the transduction portion 18, the density and modulus of elasticity of the material used to manufacture the end-bell 20 and the fore-bell 22, and the resonant frequency of the ultrasonic transducer 14. The fore-bell 22 may be tapered inwardly from its proximal end to its distal end to amplify the ultrasonic vibration amplitude as the velocity transformer 28, or alternately may have no amplification. A suitable vibrational frequency range may be about 20 Hz to 120 kHz and a well-suited vibrational frequency range may be about 30-100 kHz. A suitable operational vibrational frequency may be approximately 55.5 kHz, for example.

Piezoelectric elements 32 may be fabricated from any suitable material, such as, for example, lead zirconate-titanate, lead meta-niobate, lead titanate, barium titanate, or other piezoelectric ceramic material. Each of positive electrodes 34, negative electrodes 36, and the piezoelectric elements 32 has a bore extending through the center. The positive and negative electrodes 34 and 36 are electrically coupled to wires 38 and 40, respectively. The wires 38 and 40 are encased within a cable 42 and electrically connectable to the ultrasonic signal generator 12 of the ultrasonic system 10.

The ultrasonic transducer 14 of the acoustic assembly 24 converts the electrical signal from the ultrasonic signal generator 12 into mechanical energy that results in primarily a standing acoustic wave of longitudinal vibratory motion of the ultrasonic transducer 14 and the end effector 50 at ultrasonic frequencies. In another embodiment, the vibratory motion of the ultrasonic transducer may act in a different direction. For example, the vibratory motion may comprise a local longitudinal component of a more complicated motion of the tip of the ultrasonic system 10. A suitable generator is available as model number GEN04, from Ethicon Endo-Surgery, Inc., Cincinnati, Ohio. When the acoustic assembly 24 is energized, a vibratory motion standing wave is generated through the acoustic assembly 24. The ultrasonic system 10 is designed to operate at a resonance such that an acoustic standing wave pattern of predetermined amplitude is produced. The amplitude of the vibratory motion at any point along the acoustic assembly 24 depends upon the location along the acoustic assembly 24 at which the vibratory motion is measured. A minimum or zero crossing in the vibratory motion standing wave is generally referred to as a node (i.e., where motion is minimal), and a local absolute value maximum or peak in the standing wave is generally referred to as an anti-node (i.e., where local motion is maximal). The distance between an anti-node and its nearest node is one-quarter wavelength ($\lambda/4$).

The wires 38 and 40 transmit an electrical signal from the ultrasonic signal generator 12 to the positive electrodes 34 and the negative electrodes 36. The piezoelectric elements 32 are energized by the electrical signal supplied from the ultrasonic signal generator 12 in response to an actuator 44, such as a foot switch, for example, to produce an acoustic standing wave in the acoustic assembly 24. The electrical signal causes disturbances in the piezoelectric elements 32 in the form of repeated small displacements resulting in large alternating compression and tension forces within the material. The repeated small displacements cause the piezoelectric elements 32 to expand and contract in a continuous manner along the axis of the voltage gradient, producing longitudinal waves of ultrasonic energy. The ultrasonic energy is transmitted through the acoustic assembly 24 to the single element end effector such as the blade 50 via a transmission component or an ultrasonic transmission waveguide 104.

In order for the acoustic assembly 24 to deliver energy to the single element end effector 50, all components of the acoustic assembly 24 must be acoustically coupled to the blade 50. The distal end of the ultrasonic transducer 14 may be acoustically coupled at the surface 30 to the proximal end of the ultrasonic transmission waveguide 104 by a threaded connection such as a stud 48.

The components of the acoustic assembly 24 are preferably acoustically tuned such that the length of any assembly is an integral number of one-half wavelengths ($n\lambda/2$), where the wavelength $\lambda$ is the wavelength of a pre-selected or operating longitudinal vibration drive frequency $f_d$ of the acoustic assembly 24. It is also contemplated that the acoustic assembly 24 may incorporate any suitable arrangement of acoustic elements.

The blade 50 may have a length substantially equal to an integral multiple of one-half system wavelengths ($n\lambda/2$). A distal end 52 of the blade 50 may be disposed near an antinode in order to provide the maximum longitudinal excursion of the distal end. When the transducer assembly is energized, the distal end 52 of the blade 50 may be configured to move in the range of, for example, approximately 10 to 500 microns peak-to-peak, and preferably in the range of about 30 to 150 microns at a predetermined vibrational frequency of 55 kHz, for example.

The blade 50 may comprise features to reduce misting. For example, the blade 50 may comprise a tapered concave surface at the distal end 52, a coating formed at the distal end 52, a lumen fluidically coupled to a spraying mechanism, a material to hold an electric charge, or any combination thereof.

The blade 50 may be coupled to the ultrasonic transmission waveguide 104. The blade 50 and the ultrasonic transmission waveguide 104 as illustrated are formed as a single unit construction from a material suitable for transmission of ultrasonic energy. Examples of such materials include Ti6Al4V (an alloy of Titanium including Aluminum and Vanadium), Aluminum, Stainless Steel, or other suitable materials. Alternately, the blade 50 may be separable (and of differing composition) from the ultrasonic transmission waveguide 104, and coupled by, for example, a stud, weld, glue, quick connect, or other suitable known methods. The length of the ultrasonic transmission waveguide 104 may be substantially equal to an integral number of one-half wavelengths ($n\lambda/2$), for example. The ultrasonic transmission waveguide 104 may be preferably fabricated from a solid core shaft constructed out of material suitable to propagate ultrasonic energy efficiently, such as the titanium alloy discussed above (i.e., Ti6Al4V) or any suitable aluminum alloy, or other alloys, for example.

The ultrasonic transmission waveguide 104 comprises a longitudinally projecting attachment post 54 at a proximal end to couple to the surface 30 of the ultrasonic transmission waveguide 104 by a threaded connection such as the stud 48. In the embodiment illustrated in FIG. 1, the ultrasonic transmission waveguide 104 includes a plurality of stabilizing silicone rings or compliant supports 56 positioned at a plurality of nodes. The silicone rings 56 dampen undesirable vibration and isolate the ultrasonic energy from an outer sheath 58 assuring the flow of ultrasonic energy in a longitudinal direction to the distal end 52 of the blade 50 with maximum efficiency.

As shown in FIG. 1, the outer sheath 58 protects a user of the ultrasonic surgical instrument 10, 100 and a patient from the ultrasonic vibrations of the ultrasonic transmission waveguide 104. The sheath 58 generally includes a hub 62 and an elongated tubular member 64. The tubular member 64 is attached to the hub 62 and has an opening extending longitudinally therethrough. The sheath 58 is threaded onto the distal end of the housing 16. The ultrasonic transmission waveguide 104 extends through the opening of the tubular member 64 and the silicone rings 56 isolate the ultrasonic transmission waveguide 104 from the outer sheath 58. The outer sheath 58 may be attached to the waveguide 104 with an isolator pin 112. The hole in the waveguide 104 may occur nominally at a displacement. The waveguide 104 may screw or snap onto the hand piece assembly 60 by the stud 48. The flat portions on the hub 62 may allow the assembly to be torqued to a required level.

The hub 62 of the sheath 58 is preferably constructed from plastic and the tubular member 64 is fabricated from stainless steel. Alternatively, the ultrasonic transmission waveguide 104 may comprise polymeric material surrounding it to isolate it from outside contact.

The distal end of the ultrasonic transmission waveguide 104 may be coupled to the proximal end of the blade 50 by an internal threaded connection, preferably at or near an antinode. It is contemplated that the blade 50 may be attached to the ultrasonic transmission waveguide 104 by any suitable means, such as a welded joint or the like. Although the blade 50 may be detachable from the ultrasonic transmission waveguide 104, it is also contemplated that the single element end effector (e.g., the blade 50) and the ultrasonic transmission waveguide 104 may be formed as a single unitary piece.

Figure 1B:
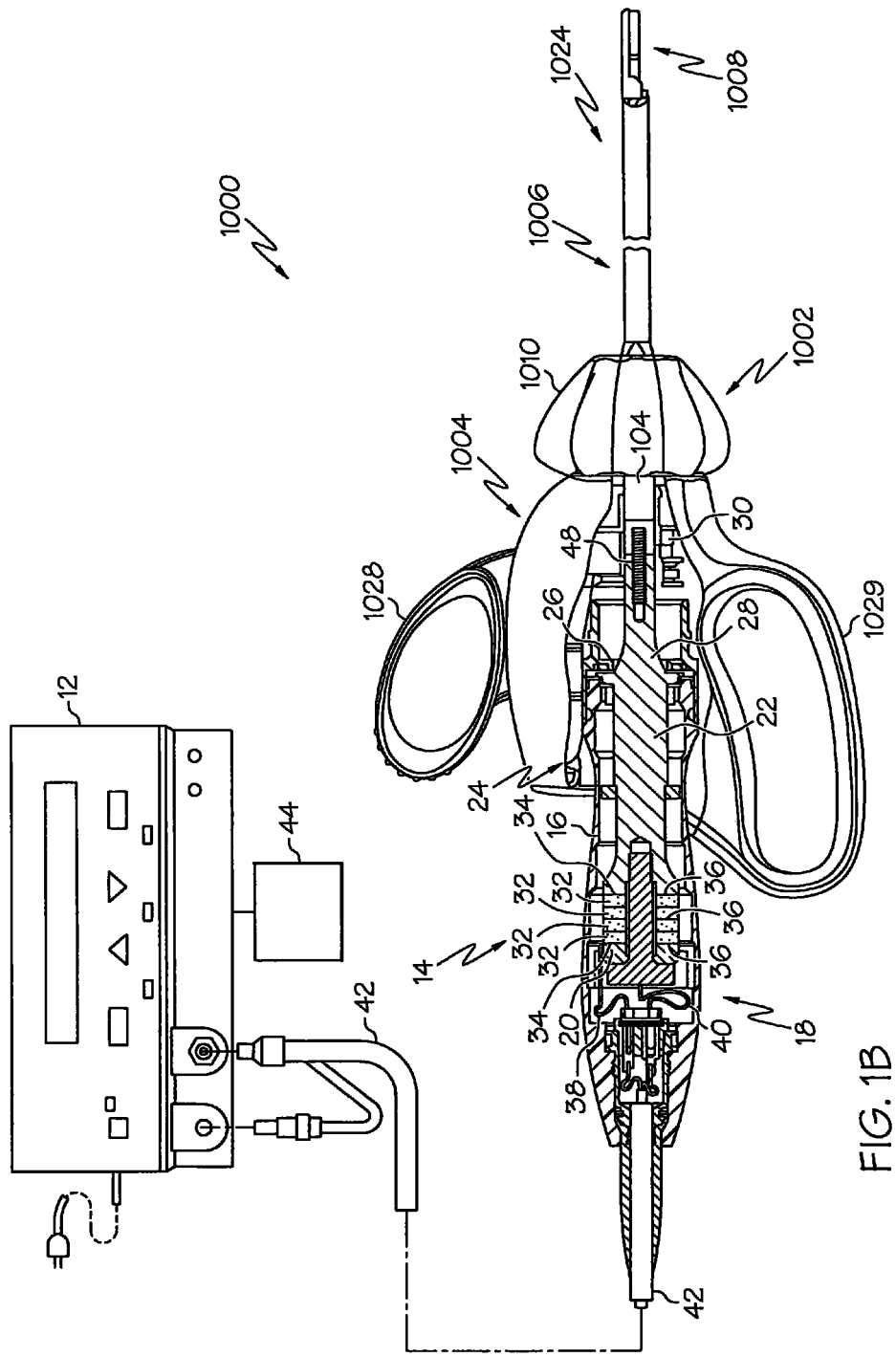
FIG. 1B illustrates one embodiment of an ultrasonic system comprising a multi-element end effector.

FIG. 1B illustrates one embodiment of an ultrasonic system 1000 comprising a multi-element end effector. One embodiment of the ultrasonic system 1000 comprises the ultrasonic generator 12 coupled to the ultrasonic transducer 14 described with reference to FIG. 1A. The ultrasonic transducer 14 is coupled to clamped coagulating shears 1002 comprising an instrument housing 1004. The acoustic assembly 18 delivers energy to the end effector 1016 (FIG. 3B) of the multi-element end assembly 1008 of the multi-element instrument. In order for the acoustic assembly 18 to deliver energy to the multi-element end effector or multi-element end assembly 1008, all components of the acoustic assembly 18 must be acoustically coupled to the ultrasonically active portions of the clamped coagulating shears 1002. Accordingly, the distal end of the ultrasonic transducer 14 may be acoustically coupled at the surface 30 to the proximal end of the ultrasonic transmission waveguide 104 by the threaded connection stud 48.

As previously discussed with reference to the ultrasonic system 10 shown in FIG. 1A, the components of the acoustic assembly 18 are preferably acoustically tuned such that the length of any assembly is an integral number of one-half wavelengths ($n\lambda/2$), where the wavelength $\lambda$ is the wavelength of a pre-selected or operating longitudinal vibration drive frequency $f_d$ of the acoustic assembly 18. The acoustic assembly 18 may incorporate any suitable arrangement of acoustic elements.

Figure 2:
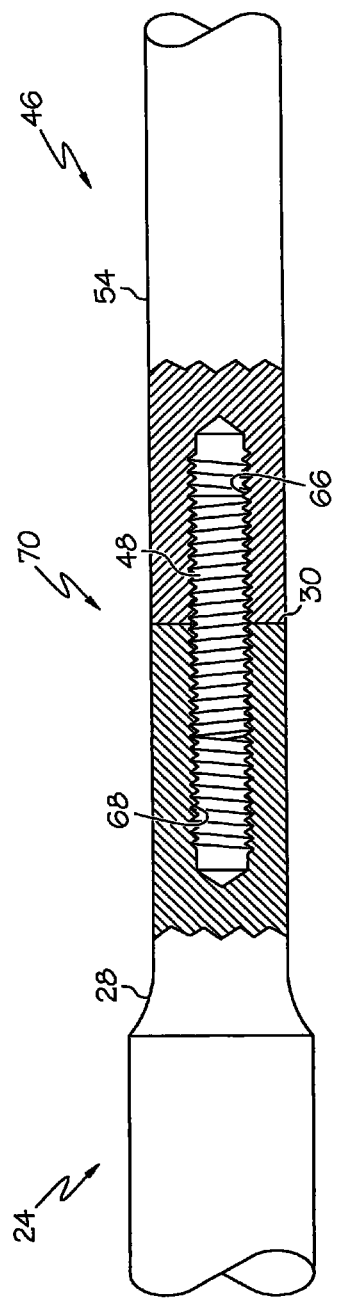
FIG. 2 illustrates one embodiment of a connection union/joint for an ultrasonic instrument.

FIG. 2 illustrates one embodiment of a connection union/joint 70 for an ultrasonic instrument. The connection union/joint 70 may be formed between the attachment post 54 of the ultrasonic transmission waveguide 104 and the surface 30 of the velocity transformer 28 at the distal end of the acoustic assembly 24. The proximal end of the attachment post 54 comprises a female threaded substantially cylindrical recess 66 to receive a portion of the threaded stud 48 therein. The distal end of the velocity transformer 28 also may comprise a female threaded substantially cylindrical recess 68 to receive a portion of the threaded stud 40. The recesses 66, 68 are substantially circumferentially and longitudinally aligned. In another embodiment (not shown), the stud is an integral component of the end of the ultrasonic transducer. For example, the treaded stud and the velocity transformer may be of a single unit construction with the stud projecting from a distal surface of the velocity transformer at the distal end of the acoustic assembly. In this embodiment, the stud is not a separate component and does not require a recess in the end of the transducer.

Figure 3A:
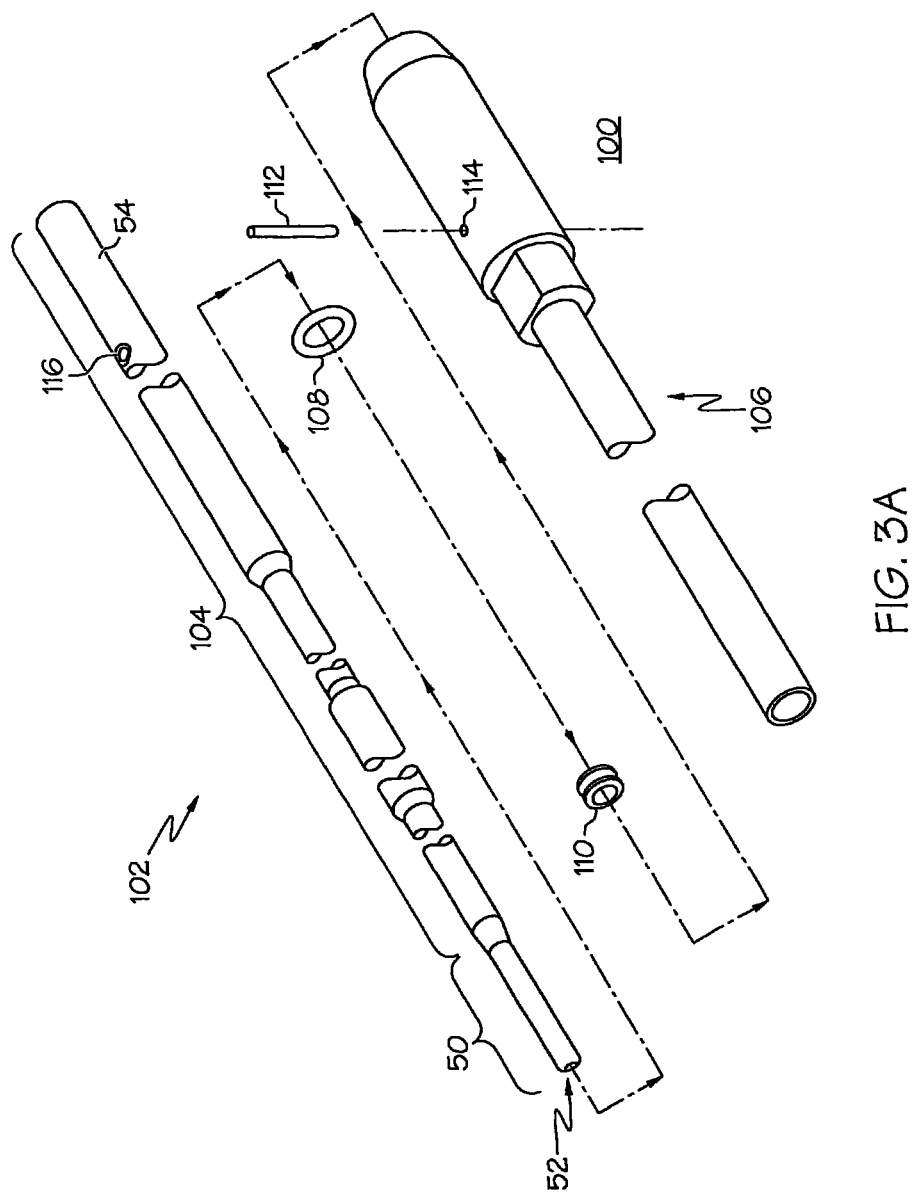
FIG. 3A illustrates an exploded perspective view of one embodiment of a single element end effector ultrasonic surgical instrument that may be coupled to the ultrasonic system illustrated in FIG. 1A.

FIG. 3A illustrates an exploded perspective view of one embodiment of a single element end effector ultrasonic surgical instrument 100. The ultrasonic surgical instrument 100 may be employed with the ultrasonic system 10 illustrated in FIG. 1A. However, as described herein, those of ordinary skill in the art will understand that the various embodiments of the ultrasonic surgical instruments disclosed herein as well as any equivalent structures thereof could conceivably be effectively used in connection with other known ultrasonic surgical instruments without departing from the scope thereof. Thus, the protection afforded to the various ultrasonic surgical blade embodiments disclosed herein should not be limited to use only in connection with the exemplary ultrasonic surgical instrument described above.

In the embodiment illustrated in FIG. 3A, the elongated transmission component is shown as the ultrasonic waveguide 104 and the end effector is shown as a single element end effector or blade 50 suitable to cut and/or coagulate tissue. The blade 50 may be symmetrical or asymmetrical.

The length of the blade 50 may be substantially equal to an integral multiple of one-half system wavelengths (nλ/2). The distal end 52 of the blade 50 may be disposed near an antinode in order to provide the maximum longitudinal excursion of the distal end 52. When the transducer assembly is energized, the distal end 52 of the blade 50 may be configured to move in the range of, for example, approximately 10 to 500 microns peak-to-peak, and preferably in the range of about 30 to 150 microns at a predetermined vibrational frequency.

The blade 50 may be coupled to the ultrasonic transmission waveguide 104. The blade 50 and the ultrasonic transmission guide 104 as illustrated are formed as a single unit of construction from a material suitable for transmission of ultrasonic energy such as, for example, Ti6Al4V (an alloy of titanium including aluminum and vanadium), aluminum, stainless steel, other known materials, or combinations thereof. Alternately, the blade 50 may be separable (and of differing composition) from the ultrasonic transmission waveguide 104, and coupled by, for example, a stud, weld, glue, quick connect, or other suitable known methods. The length of the ultrasonic transmission waveguide 104 may be substantially equal to an integral number of one-half system wavelengths (nλ/2), for example. The ultrasonic transmission waveguide 104 also may be preferably fabricated from a solid core shaft constructed out of material that propagates ultrasonic energy efficiently, such as titanium alloy (e.g., Ti6Al4V) or an aluminum alloy, for example. The ultrasonic transmission waveguide 104 also may be fabricated from a hollow core shaft constructed out of similar materials. The ultrasonic transmission waveguide 104 also may be fabricated with a combination solid/hollow core shaft, for example, a solid core shaft with hollow cavities positioned at various locations along the length of the shaft.

In the embodiment illustrated in FIG. 3A, the ultrasonic transmission waveguide 104 is positioned within the outer sheath 58 by a mounting O-ring 108 and a sealing ring 110. In other embodiments, one or more additional dampers or support members (not shown) also may be included along the ultrasonic transmission waveguide 104. The ultrasonic transmission waveguide 104 is affixed to the outer sheath 58 by the mounting pin 112 that passes through mounting holes 114 in the outer sheath 58 and a mounting hole 116 formed in the ultrasonic transmission waveguide 104.

FIG. 3B illustrates one embodiment of the clamped coagulating shears 1002 comprising a multi-element end effector as shown in FIG. 1B. FIG. 3C illustrates a perspective view of the multi-element end effector as shown in FIGS. 1B and 3B. With reference to FIGS. 1B, 3B and 3C, the clamped coagulating shears 1002 may be preferably attached to and removed from the acoustic assembly 18 as a unit. The proximal end of the clamped coagulating shears 1002 preferably acoustically couples to the distal surface 30 of the acoustic assembly 18. The clamped coagulating shears 1002 may be coupled to the acoustic assembly 18 by any suitable means.

The clamped coagulating shears 1002 preferably includes an instrument housing 1004 and an elongated member 1006. The elongated member 1006 may be selectively rotated with respect to the instrument housing 1004. The instrument housing 1004 includes a pivoting handle portion 1028 and a fixed handle portion 1029.

An indexing mechanism (not shown) is disposed within a cavity of the instrument housing 1004. The indexing mechanism is preferably coupled or attached on an inner tube 1014 to translate movement of the pivoting handle portion 1028 to linear motion of the inner tube 1014 to open and close the multi-element end assembly 1008. When the pivoting handle portion 1028 is moved toward the fixed handle portion 1029, the indexing mechanism slide the inner tube 1014 rearward to pivot the multi-element end assembly 1008 into a closed position. The movement of the pivoting handle portion 1028 in the opposite direction slides the indexing mechanism to displace the inner tube 1014 in the opposite direction, i.e., forwardly, and hence pivot the multi-element end assembly 1008 into its open position in the direction indicated by arrow 1020 as shown in FIG. 3B.

The pivoting handle portion 1028 includes a thumb loop 1030. A pivot pin 1032 is disposed through a first hole of the pivoting handle portion 1028 to allow pivoting as shown by arrow 1034 in FIG. 3B. As the thumb loop 1030 of the pivoting handle portion 1028 is moved in the direction of arrow 1034, away from the instrument housing 1004, the inner tube 1014 slides rearward to pivot the multi-element end assembly 1008 into a closed position.

The elongated member 1006 of the clamped coagulating shears 1002 extends from the instrument housing 1004. The elongated member 1006 preferably includes an outer member or outer tube 1012, an inner member or inner tube 1014, and a transmission component or ultrasonic transmission waveguide 104.

The multi-element end effector or multi-element end assembly 1008 includes a clamp arm assembly 1018, a tissue pad 1036, and an ultrasonic blade 1016. The clamp arm assembly 1018 is pivotally mounted about a pivot pin (not shown) to rotate in the direction indicated by arrow 1038. The ultrasonic blade 1016 comprises a tapered concave surface 1040 extending inwardly into the blade body.

The ultrasonic surgical instrument 100 and the clamped coagulating shears 1002 may be sterilized by methods known in the art such as, for example, gamma radiation sterilization, Ethelyne Oxide processes, autoclaving, soaking in sterilization liquid, or other known processes. In the embodiment illustrated in FIGS. 1A and 3A, an ultrasonic transmission assembly 102 of the surgical instrument 100 includes the single element ultrasonically actuated end effector or blade 50 coupled to the ultrasonic transmission waveguide 104. The blade 50 and the ultrasonic transmission waveguide 104 are illustrated as a single unit construction from a material suitable for transmission of ultrasonic energy as previously discussed (e.g., Ti6Al4V, Aluminum, Stainless Steel, or other known materials). Alternately, the blade 50 may be separable (and of differing composition) from the ultrasonic transmission waveguide 104, and coupled by, for example, a stud, weld, glue, quick connect, or other known methods. In the embodiment illustrated in FIGS. 1B and 3B, the ultrasonic transmission assembly 1024 of the clamped coagulating shears 1002 includes the multi-element end assembly 1008 coupled to the ultrasonic transmission waveguide 104. The length of the ultrasonic transmission waveguide 104 may be substantially equal to an integral number of one-half system wavelengths (nλ/2), for example. The ultrasonic transmission waveguide 104 may be preferably fabricated from a solid core shaft constructed out of material that propagates ultrasonic energy efficiently, such as titanium alloy (i.e., Ti6A14V) or an aluminum alloy, for example.

FIGS. 4-22 illustrate various embodiments of ultrasonic blades, which may be considered different embodiments of the single element end effector or the blade 50 or the ultrasonic blade 1016 of the multi-element end assembly 1008 and are generally well-suited for cutting, coagulating, and reshaping tissue. In addition, these blades comprise mist reducing features. The ultrasonic blades may be employed in the above-described ultrasonic systems 10, 1000. Those skilled in the art will appreciate that although the various embodiments of the ultrasonic blades 50, 1016 are well-suited for cutting, coagulating, reshaping tissue, and reducing the mist associated with the previously discussed functions, these ultrasonic blades are multifunctional and may be employed in multiple numerous applications.

Figure 4:
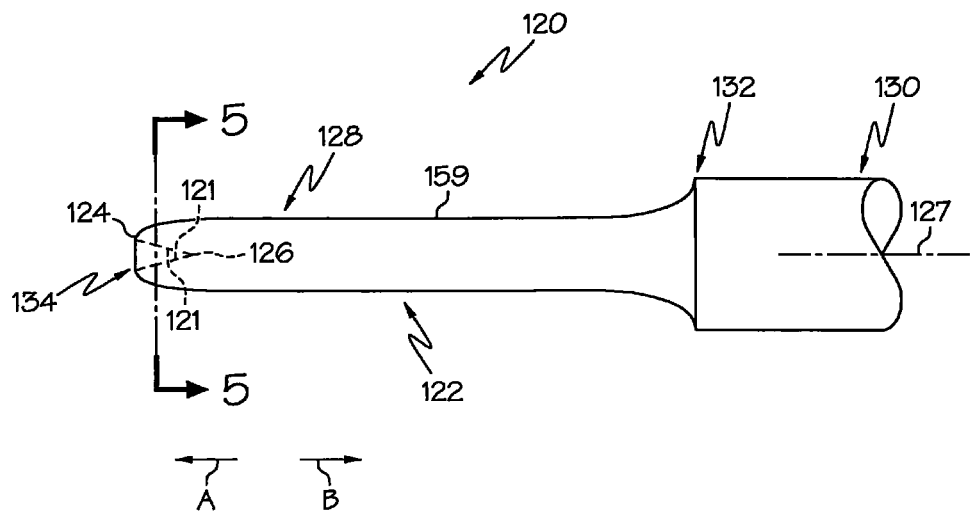
FIGS. 4-6 illustrate one embodiment of an ultrasonic blade, where.
Figure 5:
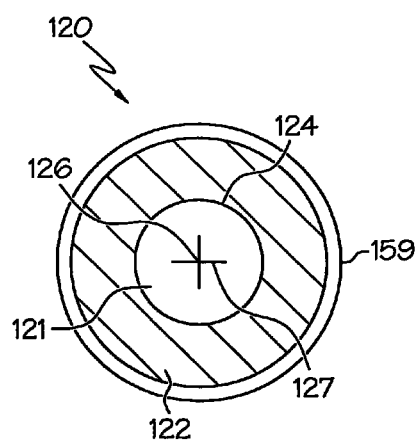
Figure 6:
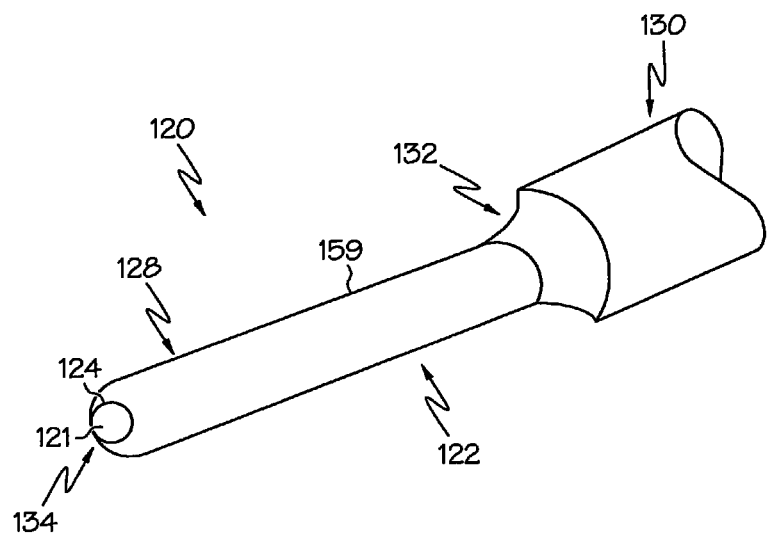

FIGS. 4-6 illustrate one embodiment of an ultrasonic blade 120. The ultrasonic blade 120 is generally well-suited for cutting, coagulating, and reshaping tissue. The ultrasonic blade 120 may be employed in various other therapeutic procedures. The ultrasonic blade 120 comprises mist reducing features as described herein. FIG. 4 is a side view of one embodiment of the ultrasonic blade 120. FIG. 5 is a cross-sectional view of one embodiment of the ultrasonic blade 120 taken along line 5-5 in FIG. 4. FIG. 6 is a perspective view of one embodiment of the ultrasonic blade in FIG. 4.

In the embodiment illustrated in FIGS. 4-6, the ultrasonic blade 120 comprises a blade body 122 having a proximal end 132 and a distal end 134. As shown in the cross-sectional view of FIG. 5, the body 122 may have a substantially circular cross section. The blade body 122 may extend along a longitudinal central axis 127. The blade body 122 may comprise a tapered concave surface 121 at the distal end 134 of the blade body 122 which may extend inwardly into the blade body 122. This inward extension may occur such that the blade body has an inwardly tapered concave shaped tip as opposed to a conventional convex shaped tip that extends outwardly or a flat faced tip. The blade body 122 may comprise a substantially elongated treatment region 128 and a neck or transition portion 130 that protrudes from the proximal end 132 of the treatment region 128. The neck portion 130 may be configured to attach to the ultrasonic transmission waveguide 104 by a stud, weld, glue, quick connect, or other suitable attachment methods, for example. In various other embodiments, the ultrasonic blade 120 and the ultrasonic transmission waveguide 104 may be formed as a single unitary body. In either configuration, the ultrasonic transmission waveguide 104 may have gain steps to amplify the mechanical vibrations transmitted to the ultrasonic blade 120 as is well known in the art. The ultrasonic blade 120 is adapted to couple to the ultrasonic transmission waveguide 104, which may be employed with the above-described ultrasonic surgical system 10.

In various embodiments, the tapered concave surface 121 may extend inwardly into the blade body 122 from a first edge 124 which may be located at the distal end 134 of the blade body 122. As previously discussed, the surface 121 may be substantially concave and may be tapered inwardly into the blade body 122. In one embodiment, as illustrated in FIG. 20, the concave surface 121 may comprise a convex portion 123 or "bump" within the concave surface 121. FIG. 20 is a side view of an ultrasonic blade 720 with the convex portion 123 formed within the concave surface 121. For example, the substantially concave surface may have a convex portion 123 or "bump" extending in a direction different from the inward direction of the extension of the surface 121 (see FIG. 20, for example).

The tapered concave surface 121 may be configured to produce a substantially convergent jet 135 of fluid mist, as shown in FIGS. 14A, B, for example. FIG. 14A is a side view of an ultrasonic blade comprising a tapered concave blade tip depicting the convergent jet 135 of fluid mist emanating from the distal end of the blade 120 in direction A. FIG. 14B is a detail view of the convergent jet 135 of fluid mist. The convergent jet 135 may be produced by the tapered concave shape of distal end 134 of the blade body 122. Fluid droplets 139 that collide with the tapered concave shape of the distal end 134 of the blade body 122 will tend to converge rather than diverge as the fluid droplets 139 travel away from the distal end 134 of the blade body 122 in the direction of arrow A. Generally, when the fluid droplets 139 collide with a convex shaped blade tip, the fluid particles 139 tend to produce a substantially divergent jet of fluid mist 137, as shown in FIG. 13A, B, for example. FIG. 13A is a side view of an ultrasonic blade 820 with a convex blade tip depicting a typical divergent jet 137 of fluid mist. FIG. 13B is a detail view of the divergent jet 137 of fluid mist. For example, when fluid particles associated with the surgical site collide with a convex shaped distal end of a blade body, the fluid mist that emanates from the distal end 134 of the blade body in direction A, tends to produce the divergent jet 137 of fluid mist, as shown in FIG. 13A. This fluid mist may limit the visibility at the surgical site. As shown in FIG. 14B, the tapered concave surface 121 may cause the fluid droplets moving in direction A to be directed towards the longitudinal axis 127 where the fluid droplets 141 may collide and coalesce, thus increasing droplet size such that the fluid droplets 141 may drop out under the influence of gravity.

With reference now back to FIGS. 4-6, in various embodiments, the distal end 134 may comprise a first edge 124. The first edge 124 may form the base from which the tapered surface 121 extends inwardly into the blade body 122 in the direction B. The first edge 124 may be formed in a variety of shapes including a circle, an ellipse, a square, a rectangle, a pentagon, a hexagon or any suitable polygon. In one embodiment, as shown in FIGS. 4-6, the tapered concave surface 121 defines a conical shape extending inwardly in direction B into the blade body 122. The conical shape may comprise a cone with an apex 126 and a circular base. In other embodiments, the base may be an ellipse, or a polygon (e.g., a pyramid) and may also comprise a right cone (e.g., where a line joining the apex to the center of the base is at a right angle to the base plane) or an oblique cone (e.g., where a line joining the apex to the center of the base is not at a right angle to the base plane). The surface may terminate at the apex 126 within the blade body 122. The conical shape of the tapered concave surface 121 may be symmetrical or asymmetrical. In the embodiment illustrated in FIGS. 4-6, the conical shape is symmetric with the apex located substantially along the longitudinal axis 127. In other embodiments, the conical shape of the tapered concave surface 121 may be asymmetric with the apex 126 located between an outer edge 159 of the blade body 122 and the longitudinal axis 127. The tapered concave surface 121 may have a second length between the first edge 124 and the apex 126. The blade body 122 may have a first length between the proximal end 132 and the distal end 134. The first length may be at least three times the second length such that vibrations produced along the blade body 122 are substantially uniform to provide substantially even distribution of energy to the tissue.

Figure 7:
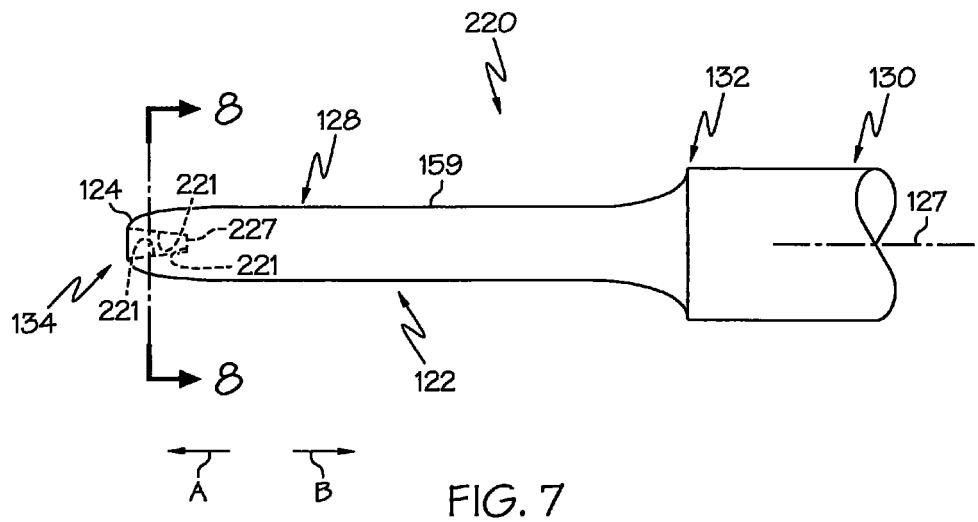
FIGS. 7-9 illustrate various embodiments of the ultrasonic blade, where.
Figure 8:
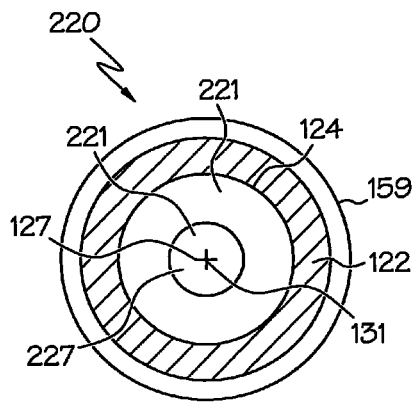
Figure 9:
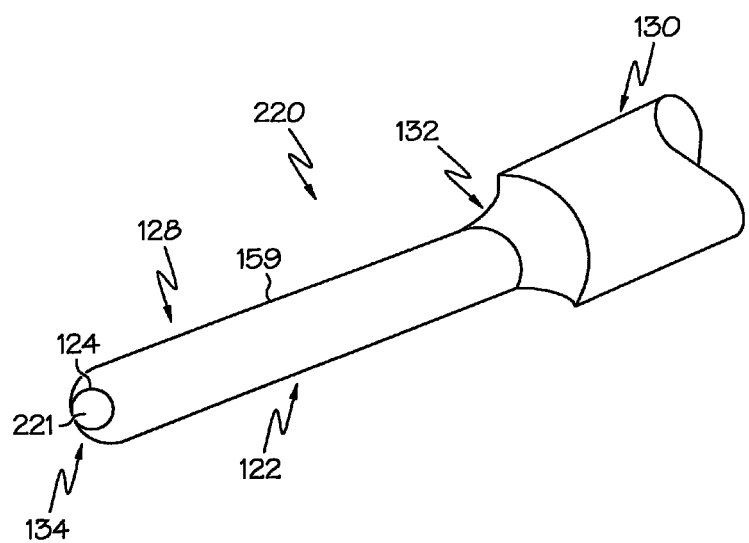

In various other embodiments, the tapered concave surface 221 of the blade body 122 may define various other symmetrical or asymmetrical shapes. In one embodiment, as shown in FIGS. 7-9, the tapered concave surface 221 may define a frusto-conical shape. FIG. 7 is a side view of another embodiment of the ultrasonic blade 220. FIG. 8 is a cross-sectional view of the ultrasonic blade 220 taken along line 8-8 in FIG.

7. FIG. 9 is a perspective view of the ultrasonic blade 220 in FIG. 7. The frusto-conical shape may extend inwardly into the blade body 122 in direction B from the first edge 124. The frusto-conical shape may comprise all of the characteristics of a cone, as defined above, but may terminate short of a hypothetical apex of the cone, in other words, the frusto-conical shape may be a shape similar to a cone but terminating in a plane 227 substantially orthogonal to the longitudinal axis 127 as opposed to a point along or near the longitudinal axis 127 found in a cone. The tapered concave surface 221 may terminate prior to reaching the hypothetical apex within the blade body 122. For example, the frusto-conical shape may be a cone with a substantially flat top as opposed to a point. In various other embodiments, the frusto-conical shape may have a rounded top or any other suitable shape for the top portion. In the embodiments illustrated in FIGS. 7-9, the frusto-conical shape of the tapered concave surface 221 is symmetric with the center 131 of the plane 227 located substantially along the longitudinal axis 127. In other embodiments, the frusto-conical shape of the tapered concave surface 221 may be asymmetric with the center 131 of the plane 227 located between an outer edge 129 of the blade body 122 and the longitudinal axis 127.

Figure 10:
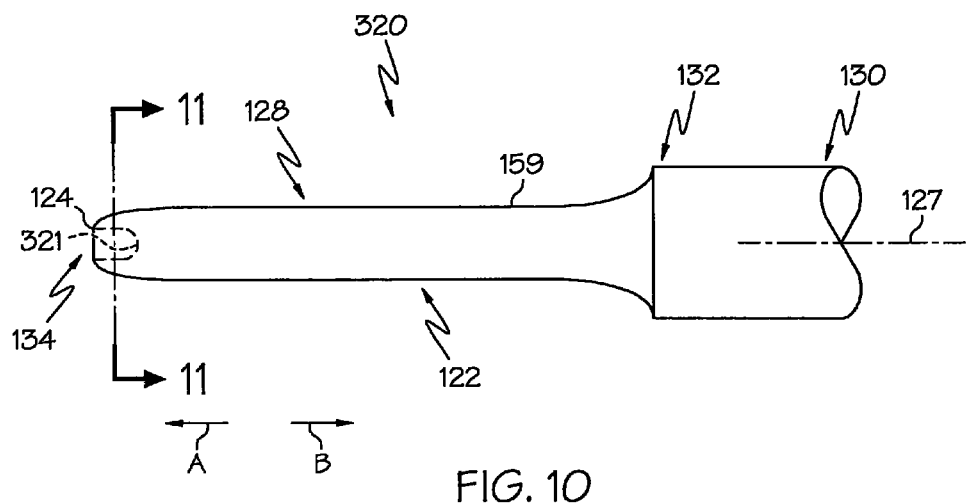
FIGS. 10-12 illustrate one embodiment of the ultrasonic blade, where.
Figure 11:
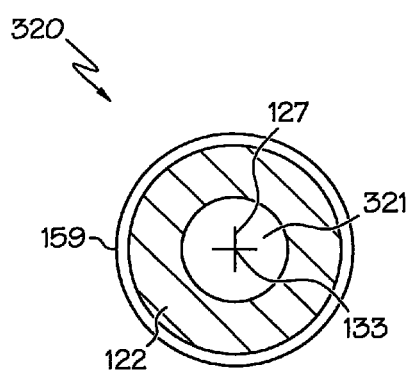
Figure 12:
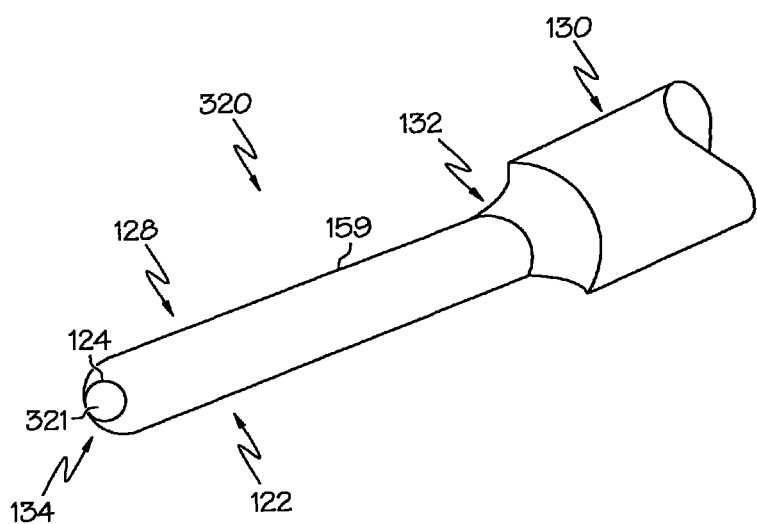

In another embodiment, as shown in FIGS. 10-12, the ultrasonic blade 320 comprises a tapered concave surface 321 defining a partial spheroid extending inwardly into the blade body 122 in the direction B. FIG. 10 is a side view of the ultrasonic blade 320. FIG. 11 is a cross-sectional view of the ultrasonic blade 320 taken along line 11-11 in FIG. 10. FIG. 12 is a perspective view of the ultrasonic blade 320 in FIG. 10. The partial spheroid may extend inwardly from the first edge 124, or base, into the blade body 122 in the direction of B. A spheroid may be formed when an ellipse or circle is rotated about an axis. For example, when a circle is rotated about its axis, a spheroid, commonly referred to in this case as a sphere, is formed. When the ellipse is rotated about its major axis a prolate spheroid is formed, and when the ellipse is rotated about its minor axis an oblate spheroid is formed. The tapered concave surface 321 may define at least one of a partial sphere, a partial prolate spheroid, or a partial oblate spheroid. The partial spheroid may be more than half of a spheroid, less than half of a spheroid, or exactly half of a spheroid (e.g., a hemispheroid). The first edge 124 may form a circle or an ellipse which has a center 133 that may be substantially aligned with the longitudinal axis 127.

In at least one embodiment, the blade may comprise a variety of shapes. For example, the blade may be curved. The blade may be curved in any direction. In addition, the blade may comprise various cross-sections. For example, the blade may comprise a square cross-section. All of these blade shapes may comprise an axis defined between the proximal end 132 and the distal end 134 of the blade.

FIG. 23 is a perspective view of an asymmetric ultrasonic blade comprising a tapered concave surface extending inwardly into the blade body. More details regarding curved or asymmetric blades are described in U.S. Pat. No. 6,283, 981, which is incorporated herein by reference. As shown in FIG. 23, the ultrasonic surgical instrument 10 may comprise an ultrasonic blade 920 and a treatment region 960 that includes a curved blade designed to cut and coagulate tissue. The treatment region 960 may be curved to provide the surgeon with better access and visibility. The treatment region 960 may also comprise a tapered concave surface 921 which may provide a mist reducing feature. As illustrated in FIG. 23, the curved treatment region may be symmetrical about x,z plane, but asymmetrical about x,y plane. The tapered concave surface 921 may extend inwardly into the blade body 922 from a first edge 924 which may extend substantially parallel to the perimeter of the blade tip 923. In other embodiments, the first edge may be a different shape from the perimeter of the blade tip. For example, the first edge may form a circle when the perimeter of the blade tip forms a trapezoid. The embodiments are not limited in this context.

As previously discussed, in various embodiments, the tapered concave surface may extend inwardly into the blade body 122 in direction B from a first edge 124 either symmetrically or asymmetrically. This extension may occur at or near the longitudinal central axis 127 of the blade body 122. For example, with respect to the embodiment illustrated in FIGS. 4-6, the surface may extend symmetrically to form or define a right cone or asymmetrically to form or define an oblique cone. FIG. 21 is a side view of an ultrasonic blade 820 with a tapered concave surface 821 extending inwardly into the blade body 122 asymmetrically along direction B. FIG. 22 is a cross-sectional view of the ultrasonic blade 820 taken along line 22-22 in FIG. 21. As shown in FIG. 21, the tapered concave surface 821 extends inwardly from the distal end 134 of the blade 820 to the proximal end 132 of the blade 820 to form a substantially oblique cone. The oblique cone may be formed asymmetrically about the longitudinal axis 127. For example, the apex 826 of the oblique cone may be offset from the center of the longitudinal axis 127 or the center 143 of the geometric shape formed by the first edge 124. The surface may form any geometrical shape, which may be formed asymmetrically within the blade body.

In various embodiments, as shown in FIGS. 15A-D, at least a portion 129 of the blade body 122 may comprise a layer of material 150 to minimize the divergent jet 137 of fluid mist (FIGS. 13A, B) associated with the ultrasonic blade 420. FIG. 15A is a side view of an ultrasonic blade 420 with at least a portion 129 of the ultrasonic blade 420 comprising at least one layer of the material 150 formed thereon. FIG. 15B is cross-sectional view of the ultrasonic blade 420 taken along line 15B-15B in FIG. 15A. FIG. 15C is a detailed view of the ultrasonic blade 420 of FIG. 15A. The coated portion 129 of the blade body 122 may be located at the distal end 134 of the ultrasonic blade 420. The coated portion 129 of the blade body 122 may comprise at least one layer of a material 150 which acts to globulize fluid particles 152 when they contact the coated portion 129 of the blade body 122. To globulize refers to creating globules or forming droplets of fluid. The material 150 may have properties which cause the material 150 to repel fluid. For example, the material 150 may be hydrophobic and thus repel fluid which may include irrigation saline, interstitial fluid, blood plasma and a cell.

The gobulization of the fluid may be caused by differences between the surface tension of the material 150 and the surface tension of the fluid in contact with the material 150. The material 150 may have a surface tension which is less than the surface tension of the fluid which may cause the fluid to globulize on the surface of the material 150. A fluid may form globules or "beads" on surfaces coated with a material where the surface tension of the material 150 on the surface 156 is less than the surface tension of the fluid. The formation of globules may prevent the "wetting" or formation of a layer of fluid spreading over the surface of the coated portion 129 of the blade body 122. The globules 152 may be pushed off of the blade body 122 through the vibrating motion of the end effector 50 unlike a layer of fluid which may have to be atomized from the surface thus causing a mist to form. The effects of the differences between the surface tension of the material 150 and the surface tension of the fluid may be illustrated in terms of a contact angle formed between a fluid interface and a surface.

FIG. 15D illustrates a contact angle 156 formed between a fluid interface 157 and a surface 158 of the ultrasonic blade 122 of FIG. 15A. As shown in FIG. 15D, the contact angle 156 is the angle at which the fluid interface 157 meets the surface 158 of the material 150. The contact angle 156 is specific for any given system and is determined by the interactions across the three interfaces. For clarity, the concept is illustrated with a small liquid droplet resting on a flat horizontal solid surface. On extremely hydrophilic surfaces, a water droplet will completely spread (an effective contact angle of 0°). This occurs for surfaces that have a large affinity for water (including materials that absorb water). On many hydrophilic surfaces, water droplets will exhibit contact angles of 10° to 30°, for example. On highly hydrophobic surfaces, which are incompatible with water, one may observe a large contact angle (70° to 90°). Some surfaces have water contact angles as high as 150° or even nearly 180°. On these surfaces, water droplets simply rest on the surface, without actually wetting the surface to any significant extent, for example. These surfaces are termed superhydrophobic and can be obtained on fluorinated surfaces (TEFLON®-like coatings) that have been appropriately micropatterned. The contact angle 156 thus directly provides information on the interaction energy between the surface 156 of the material 150 and the fluid.

In various embodiments, the surface 158 of the material 150 may be hydrophobic or superhydrophobic. The first material 150 may comprise any one of polytetrafluoroethylene (TEFLON®), polypropylene, polyethylene, waxes, polycaprolactone, any combination thereof, or any other suitable hydrophobic or superhydrophobic material. For example, the first material 150 may comprise at least one of a polypropylene wax hydrocarbon mixture or TEFLON®. The first material 150 may be applied to the surface through a variety of coating techniques including dipping, spraying, brushing, drying, melting, sintering, fused curing, and any other suitable method for applying hydrophobic materials. Other methods for applying hydrophobic materials may include material deposition techniques that are well known in the art. More details regarding hydrophobic and superhydrophobic materials and methods for applying those materials to a surface are described by U.S. Pat. No. 7,041,088 and U.S. Pat. No. 6,663,941, which are incorporated herein by reference.

In various other embodiments, as shown in FIGS. 16-17, at least a portion of the blade body 122 may be coated with at least two materials which may allow an electric charge to be carried by at least one of the materials. FIG. 16 is a side view of an ultrasonic blade 520 with portions of the blade body 122 coated with more than one material to provide an electric charge to the distal end 134 of the blade body 122. FIG. 17 is cross-sectional view of the ultrasonic blade 520 taken along line 17-17 in FIG. 16. At least a first portion 129 of the blade body 122 may comprise at least one layer of a first material 160. This first material 160 may contact at least a portion of a second material 162. The first material 160 may comprise a material suitable to carry an electric charge. The electric charge carried by the first material 160 may be the same as the nominal electric charge carried by the fluid. The similar electric charges may cause the portion 129 of the blade body 122 covered with the first material to repel the fluid. For example, if the first material 160 has a positive charge and the fluid has a positive charge, the fluid will be repelled by the first material 160. Accordingly, the first material 160 acts as a hydrophobic surface. The first material 160 may receive its electrical charge carried by wires from an electrical source located at or near the proximal end 132 of the blade body 122. For example, the electrical source may comprise a direct current ("DC") electrical source (e.g., a battery). In another embodiment, the electrical source may be located in a different location. The wires may be provided within a bore formed in the ultrasonic blade 520 or maybe provided along the outside of the ultrasonic blade 520 within a channel or conduit. The misting effect may be reduced because the fluid is repelled from the surface of the first material 160. Accordingly, there is minimal fluid on the surface of the blade body 122 to be atomized by the ultrasonically activated blade 520.

At least a second portion of the blade body 122 comprises at least one layer of a second material 162. The second material 162 may comprise an electrically insulative material. The second material 162 may be located between the first material 160 and the blade body 122. The second material 162 may insulate the blade 520, and the blade body 122, from electrical charges. The second material 162 may be an electret material which may be made from silicon dioxide, fluoropolymer, polypropylene or any other suitable material. These materials may hold a constant or slow decaying charge. The first material 160 may be a metallic layer or a vapor deposited layer acting as a floating conductor wherein wires may not be required to convey a charge to the second material 162 from an electrical source.

In another embodiment, the electric charge carried by the first material 160 may be the opposite polarity as the nominal electric charge carried by the fluid. The opposite electric charges may cause the portion 129 of the blade body 122 covered with the first material to attract the fluid. For example, if the first material 160 has a negative charge and the fluid has a positive charge, the fluid will be attracted by the first material 160. Accordingly, the first material 160 acts as a hydrophilic surface. Accordingly, electric charge on the coating materials may be selected such that they exhibit opposite charges to that of the fluid to create attraction rather than repulsion between the blade body 122 and the fluid. This may enable surgical "smoke" or mist to globulize as it collects on the surface of the blade body 122. In addition, this technique may be employed to attract other materials or constituents, such as, drug molecules, fibrin, and natural adhesives to the treatment site. These other materials or constituents may be introduced in a liquid suspension. The difference in charges between the blade body 12 ad the fluid would act to concentrate these other materials or constituents in the vicinity of the distal end of the blade body 122.

In various embodiments, as shown in FIGS. 18-19, a blade 620 may comprise a bore 180 (e.g., a lumen). FIG. 18 is a side view of the ultrasonic blade 620 with a longitudinally extending bore 180. FIG. 19 is cross-sectional view of the ultrasonic blade 620 taken along line 19-19 in FIG. 18. The bore 180 may extend longitudinally along the longitudinal axis 127, or, in certain embodiments, the bore may extend in a different direction. The bore 180 may be formed within the blade 620. The ultrasonic blade 620 may be configured to emit a spray via the bore 180 in a direction indicated by arrow 640 at the distal end 134 of the blade 620. The spray may emanate from a spray source 161 located at or near the proximal end 132 of the blade 620 and travel in the flow direction 640. The flow direction 640 may be from the proximal end 132 to the distal end of the blade 620. In another embodiment, the spray source 161 may be found in other locations. The spray emanating from the distal end 134 of the blade 620 may substantially prevent fluid from contacting the distal end 134 of the blade 620. This prevention of contact may reduce the mist as a layer of fluid may not be present on the blade 620 for atomization. The spray may comprise a gas. For example, the gas may be carbon dioxide, air or some other suitable gas.

The ultrasonic blade 120 comprises a treatment region 128 that is suitable to effect tissue, such as, for example, cut, coagulate, reshape, scrape, and remove tissue. A distal end 134 of the treatment region 128 may also comprise a tip with a cutting edge. Additional cutting edges may be positioned laterally along both sides of the treatment region 128. In one embodiment, the cutting edges extend from the proximal end 132 to the distal end 134 of the treatment region 128.

The ultrasonic blades as discussed herein may be fabricated from a material suitable for transmission of ultrasonic energy such as, for example, Ti6Al4V, Aluminum, Stainless Steel, or other known materials. The ultrasonic blade may be used in a single-element end effector (e.g., a scalpel, hook, or ball coagulator) as discussed with reference to ultrasonic system 10 and FIGS. 1A, 2 and 3A, or a multiple-element end effector (e.g., a clamping coagulating shears) as discussed with reference to ultrasonic system 1000 and FIGS. 1B, 3B, and 3C, for example.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam.

Although various embodiments have been described herein, many modifications and variations to those embodiments may be implemented. For example, different types of end effectors may be employed. In addition, combinations of the described embodiments may be used. For example, a concave blade tip may be coated with a hydrophobic material. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
   a transducer configured to produce vibrations at a predetermined frequency; and
   an ultrasonic blade extending along a longitudinal axis coupled to the transducer, wherein the ultrasonic blade comprises:
      a substantially solid, substantially cylindrical body without a channel formed from a first metallic electrically conductive material, the body having a proximal end and a distal end, wherein the distal end is movable relative to the longitudinal axis by the vibrations produced by the transducer;
      at least one annular layer of a second metallic electrically conductive material formed on at least a first portion of the body, the second metallic material being suitable to carry an electric charge from a direct current electrical source, wherein the first metallic material is different than the second metallic material; and
      at least one annular layer of a third electrically insulative material formed on at least a second portion of the body, wherein the third electrically insulative material is located intermediate the first metallic material and the second metallic material, wherein the third electrically insulative material is different than the second metallic material, wherein the third electrically insulative material comprises an electret material, and wherein the third electrically insulative material entirely encloses the first metallic material to electrically isolate the first metallic material from the second metallic material.

2. The surgical instrument of claim 1, wherein the electric charge carried by the at least one annular layer of the second metallic material is a positive charge, and wherein the ultrasonic blade is configured to be positioned by a fluid at a treatment site that has a positive electrical charge.

3. The surgical instrument of claim 1, wherein the at least one annular layer of the third electrically insulative material is to electrically insulate the blade from electrical charges.

4. The surgical instrument of claim 1, wherein the electrical charge carried by the at least one annular layer of the second metallic material is a negative charge, and wherein the ultrasonic blade is configured to be positioned by a fluid at a treatment site that has a negative electrical charge.

5. An ultrasonic surgical blade, comprising:
   a substantially solid, substantially cylindrical body without a channel formed from a first metallic electrically conductive material, the body having a proximal end and a distal end, wherein the distal end is movable relative to a longitudinal axis by vibrations produced by a transducer;
   at least one annular layer of a second metallic electrically conductive material formed on at least a first portion of the body, the second metallic material being suitable to carry an electric charge from a direct current electrical source, wherein the first metallic material is different than the second metallic material; and
   at least one annular layer of a third electrically insulative material formed on at least a second portion of the body, wherein the third electrically insulative material is located intermediate the first metallic material and the second metallic material, wherein the third electrically insulative material is different than the second metallic material, wherein the third electrically insulative material comprises an electret material, and wherein the third electrically insulative material entirely encloses the first metallic material to electrically isolate the first metallic material from the second metallic material.

6. The ultrasonic surgical blade of claim 5, wherein the electric charge carried by the at least one annular layer of the second metallic material is a positive charge, and wherein the ultrasonic blade is configured to be positioned by a fluid at a treatment site that has a positive electrical charge.

7. The ultrasonic surgical blade of claim 5, wherein the at least one annular layer of the third electrically insulative material is to electrically insulate the blade from electrical charges.

8. The surgical instrument of claim 5, wherein the electrical charge carried by the at least one annular layer of the second metallic material is a negative charge, and wherein the ultrasonic blade is configured to be positioned by a fluid at a treatment site that has a negative electrical charge.

9. A method comprising:
providing an ultrasonic surgical blade comprising a substantially solid, substantially cylindrical body without a channel formed from a first metallic electrically conductive material, the body having a proximal end and a distal end, wherein the distal end is movable relative to a longitudinal axis by vibrations produced by a transducer;
applying at least one annular layer of a second metallic electrically conductive material onto at least a portion of the body, the second metallic material comprising a material suitable to carry an electric charge from a direct current electrical source, wherein the first metallic material is different than the second metallic material; and
applying at least one annular layer of a third electrically insulative material on at least a second portion of the body, wherein the third electrically insulative material is located intermediate the first metallic material and the second metallic material, wherein the third electrically insulative material is different than the second metallic material, wherein the third electrically insulative material comprises an electret material, and wherein the third electrically insulative material entirely encloses the first metallic material to electrically isolate the first metallic material from the second metallic material.

10. A surgical instrument, comprising:
a transducer configured to produce vibrations at a predetermined frequency; and
an ultrasonic blade extending along a longitudinal axis coupled to the transducer, wherein the ultrasonic blade comprises:
a substantially solid, substantially cylindrical body without a channel and having a first length, the body comprising a proximal end and a distal end, wherein the distal end is movable relative to the longitudinal axis by the vibrations produced by the transducer;
at least one layer of a first material formed on at least a portion of the body, wherein the first material comprises a superhydrophobic material and wherein the first material is to globulize fluid particles in contact therewith to reduce a mist plume produced by fluid particles contacting a surface of the body of the ultrasonic blade when energized during an ultrasonic surgical procedure; and
a tapered inner concave surface forming a conical shape formed at the distal end extending inwardly into the substantially solid, substantially cylindrical blade body substantially along the longitudinal axis, wherein the conical shape comprises an apex within the substantially solid, substantially cylindrical blade body, wherein the tapered inner concave surface terminates at or before the apex of the conical shape, wherein the tapered inner concave surface comprises a second length between the distal end and the apex, wherein the first length is at least three times the second length such that vibrations produced along the substantially solid, substantially cylindrical blade body are substantially uniform to provide substantially even distribution of energy to the tissue, and wherein the tapered concave surface is configured to cause fluid droplets to converge along the longitudinal axis when the fluid droplets collide with the tapered concave surface to enhance visibility of the surgical site by reducing a mist plume produced by fluids contacting a surface of the energized ultrasonic blade during ultrasonic surgical procedures.

* * * * *